US008338665B2

(12) United States Patent
Gilbertson et al.

(10) Patent No.: US 8,338,665 B2
(45) Date of Patent: Dec. 25, 2012

(54) METHODS AND VECTORS FOR PRODUCING TRANSGENIC PLANTS

(75) Inventors: Larry Gilbertson, Chesterfield, MO (US); Susan Jane Johnson, Creve Coeur, MO (US)

(73) Assignee: Monsanto Technology LLC, St. Louis, MO (US)

( * ) Notice: Subject to any disclaimer, the term of this patent is extended or adjusted under 35 U.S.C. 154(b) by 509 days.

(21) Appl. No.: 12/504,646

(22) Filed: Jul. 16, 2009

(65) Prior Publication Data

US 2010/0035264 A1 Feb. 11, 2010

Related U.S. Application Data

(60) Provisional application No. 61/129,739, filed on Jul. 16, 2008.

(51) Int. Cl.
*C12N 15/84* (2006.01)
*C12N 15/113* (2010.01)
*A01H 5/00* (2006.01)

(52) U.S. Cl. ........ 800/285; 800/282; 800/294; 800/300; 435/469; 536/24.5

(58) Field of Classification Search ........................ None
See application file for complete search history.

(56) References Cited

U.S. PATENT DOCUMENTS

| | | | |
|---|---|---|---|
| 5,939,539 A | 8/1999 | Lange et al. | |
| 6,521,458 B1 | 2/2003 | Gutterson et al. | |
| 7,303,909 B2 | 12/2007 | Heim et al. | |
| 7,749,751 B2 | 7/2010 | Depicker et al. | |

FOREIGN PATENT DOCUMENTS

| | | |
|---|---|---|
| EP | 0 716 147 | 6/1996 |
| EP | 1 009 842 | 6/2000 |
| EP | 1 033 409 | 9/2000 |
| EP | 1 140 043 | 10/2001 |
| WO | 97/14807 | 4/1997 |
| WO | 99/01563 | 1/1999 |
| WO | 01/44482 A2 | 6/2001 |
| WO | WO 03/003816 A2 | 1/2003 |
| WO | 03/069980 A2 | 8/2003 |
| WO | 03/079765 | 10/2003 |
| WO | WO 2004/092390 A2 | 10/2004 |
| WO | WO 2007/134234 A2 | 11/2007 |

OTHER PUBLICATIONS

Jackson et al. Nature Biotechnology 21(6): 635-637 (2003).*
Coles et al., "Modification of gibberellin production and plant development in *Arabidopsis* by sense and antisense expression of gibberellin 20-oxidase genes," *The Plant Journal* 17(5):547-556 (1999).
Ebinuma et al., "Selection of marker-free transgenic plants using the isopentenyl transferase gene," *Proc. Natl. Acad. Sci. USA*, 94:2117-2121 (1997).
Endo et al., "Single-step transformation for generating marker-free transgenic rice using the *ipt*-type MAT vector system," *The Plant Journal* 30(1):115-122 (2002).
Fray et al., "Constitutive expression of a fruit phytoene synthase gene in transgenic tomatoes causes dwarfism by redirecting metabolites from the gibberellin pathway," *The Plant Journal* 8(5):693-701 (1995).
Hanson et al., "A simple method to enrich an *Agrobacterium*-transformed population for plants containing only T-DNA sequences," *The Plant Journal* 19(6):727-734 (1999).
Hedden, "Recent advances in gibberellin biosnythesis," *Journal of Experimental Botany* 50(334):553-563 (1999).
Hedden et al., "Gibberellin metabolism: new insights revealed by the genes," *Trends in Plant Science*, 5(12):523-530 (2000).
Lange et al., "Cloning and Expression of a Gibberellin 2β, 3 β-Hydroxylase cDNA from Pumpkin Endosperm," *The Plant Cell*, 9:1459-1467 (1997).
Romero et al., "Expression of the yeast trehalos-6-phosphate synthase gene in transgenic tobacco plants: pleiotropic phenotypes include drought tolerance," *Planta* 201:293-297 (1997).
Sonnewald et al., "Transgenic tobacco plants expressing yeast-derived invertase in either the cytosol, vacuole or apoplast: a powerful tool for studying sucrose metabolism and sink/source interactions," *The Plant Journal* 1(1):95-106 (1991).
Sugita et al., "A transformation vector for the production of marker-free transgenic plants containing a single copy transgene at high frequency," *The Plant Journal* 22(5):461-469 (2000).
Ye et al., "Altered fructan accumulation in transgenic *Lolium multiflorum* plants expressing a *Bacillus subtilis sacB* gene," *Plant Cell Reports* 20:205-212 (2001).
Ye et al., "Plant development inhibitory genes in binary vector backbone improve quality event efficiency in soybean transformation," *Transgenic Res.* 17:827-838 (2008).
Breitler et al., "A novel two T-DNA binary vector allows efficient generation of marker-free transgenic plants in three elite cultivars of rice (*Oryza saliva* L.)", *Transgenic Research, 13*:271-287 (2004).
Chen et al., "A novel T-DNA vector design for selection of transgenic lines with simple transgene integration and stable transgene expression", *Functional Plant Biology*, 32:671-681 (2005).
International Search Report, International Application No. PCT/US2009/050910 (Oct. 29, 2009).
McCormac et al., "Efficient co-transformation of *Nicotiana tabacum* by two independent T-DNAs, the effect of T-DNA size and implications for genetic separation", *Transgenic Research, 10*:143-155 (2001).

* cited by examiner

*Primary Examiner* — David T Fox
(74) *Attorney, Agent, or Firm* — Thomas P. McBride; David R. Marsh; Arnold & Porter LLP

(57) ABSTRACT

Methods of, and compositions for, assembling one or more transcription units in a genome without a linked selectable marker or other unwanted transcription unit are provided. Also provided methods of, and compositions for, assembling one or more transcription units in a genome with a reduced frequency of vector backbone.

30 Claims, 12 Drawing Sheets

SEQUENCE LISTING

<160> NUMBER OF SEQ ID NOS: 41

<210> SEQ ID NO 1
<211> LENGTH: 75
<212> TYPE: RNA
<213> ORGANISM: Artificial Sequence
<220> FEATURE:
<223> OTHER INFORMATION: Synthetic Construct

<400> SEQUENCE: 1
ucaaagucuu cacaguuaaa uaucaaaac aaguaaauag uauuauuaaa aauauaaaaa    60
ucuuauuauu acaau                                                  75

<210> SEQ ID NO 2
<211> LENGTH: 75
<212> TYPE: RNA
<213> ORGANISM: Artificial Sequence
<220> FEATURE:
<223> OTHER INFORMATION: Synthetic Construct

<400> SEQUENCE: 2
caacacaccu uaaaaauaau ucuguaauua auuaaaauac aaauaguagg uuuauauaaa   60
aauuaaauaa uuuac                                                  75

<210> SEQ ID NO 3
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 3
acgucuuaaa ccagggauuu auaaguuaaa aucacuauuu auucuauaaa aaaauauuac   60
guaacuaaaa aaauu                                                  75

<210> SEQ ID NO 4
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 4
auaauaacag guuuaaacua auuuauuaau auuaauuacu acuuuaagua aaaaauacua   60
cguuuuaaaa auagu                                                  75

<210> SEQ ID NO 5
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 5
uuauugucaa cuugauaucu cguauagcaa uagacuauua aaaauuuuau uaguaaaaau   60
uuaauauaaa aguuu                                                  75

<210> SEQ ID NO 6
<211> LENGTH: 75
<212> TYPE: RNA
<213> ORGANISM: Artificial Sequence

```
<220> FEATURE:
<223> OTHER INFORMATION: Synthetic Constructs

<400> SEQUENCE: 6
aagauauaau auuuaaaauu uauuuuaaua auuuuaauuc ccaaacguaa guacuaaaua      60
uuauuaaacu uauuu                                                      75

<210> SEQ ID NO 7
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 7
auccuaguaa acuccaaaua cacgacaaua uuuaaacuaa uuuaauauua agugcuaauu      60
uuauaauaua uauuu                                                      75

<210> SEQ ID NO 8
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 8
aacuucagaa agggauagua gacaccuucu aauagauuau auaaaauuau uauuauucu       60 uaaauuuaac uaauc                                                      75

<210> SEQ ID NO 9
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 9
cucgccucua ucuguuaauu gaauuauuaa uuauauucac uauuuuuaa aaaauauacu       60 gcuauuaauu uuagc                                                      75

<210> SEQ ID NO 10
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 10
acucuuccuc cuuucuucuu uuauaauuaa uauaaacgua auaauucuau uguuacuuau      60
uuaauacuua aauuc                                                      75

<210> SEQ ID NO 11
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 11
gaaucucaaa uauucgauaa gagauucuaa uacuuauuua aaaauuuuua caaaaauuaa      60
uauacaguaa auuua                                                      75
```

```
<210> SEQ ID NO 12
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 12
acgguuaacc uuucaaaaaa aaaaaauaca aaucuaaagu uauuucuuua uaaauuguua      60
cuuauuuucu aaacu                                                      75

<210> SEQ ID NO 13
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 13
aaauagcucu uugguuuuua ucaaauauau aauuuuauac uauuauaaau aauuacuagu      60
uagcuugugu aaaua                                                      75

<210> SEQ ID NO 14
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 14
auacaauauu uuuuauuaca auacuauauu uuaauuaauu ucuaauauua gcaaaucaaa      60
uuaaguuaua gauaa                                                      75

<210> SEQ ID NO 15
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 15
ucuucuaacg gcuucaccuu ugauauuuuu gaacugauau uaauuuuuaa auuauaaauu      60
uacaguuaau aacaa                                                      75

<210> SEQ ID NO 16
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 16
uuguucugaa auaccacuuu uauaaagaau auaaaaaauu uaguccgacu uuaauauuuu      60
auuuuaaaaa uuucc                                                      75

<210> SEQ ID NO 17
<211> LENGTH: 75
<212> TYPE: RNA
<213> ORGANISM: Artificial Sequence
<220> FEATURE:
<223> OTHER INFORMATION: Synthetic Constructs
```

```
<400> SEQUENCE: 17
aguauuuguu ugaccuuauc gauaguuuac uuguauauau uuaauacuaa auuauuaaaa    60
auacuuuucu uuuuu                                                    75

<210> SEQ ID NO 18
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 18
uacaauaacg agccgaaaau acuuuauau uaauuaaaau auuuagcuaa uaagaaguga     60
auuauaauau agcgg                                                    75

<210> SEQ ID NO 19
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 19
uuaacuuuau aauauuauau uauuuuuaag uauuauaaaa cgucuaauuu agcaaauaau    60
uaacaaauuu uacaa                                                    75

<210> SEQ ID NO 20
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 20
ccugaauccu uauugggcuc guauuuuuu auauagaaua uauuaauuua caggauaaua     60
uauuuuaauu gaaua                                                    75

<210> SEQ ID NO 21
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 21
acuuaaguga aaaguaaacu uuuucaccc uauuaacuau uuauuaaaa uuuacuuuau      60 auaacuaaau uauaa                                                    75

<210> SEQ ID NO 22
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 22
aaacgaagag aguugcuuuu uuuuauauau uguuuauauu auacguucu auaaagaauu     60 cuuauuuuau auugc                                                    75
```

<210> SEQ ID NO 23
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 23
agcuauaggg uuuguccuaa agcaaaauag ugauuuaaau uuaauaguaa aucacuaauu    60
ugauaaaaua acuuu                                                    75

<210> SEQ ID NO 24
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 24
guuuauuacg aauuugucga uauuaaacaa aacgauuagu uuuaauaau uuauaaaaaa     60 guuauauuug aauau                                                    75

<210> SEQ ID NO 25
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 25
ucucuagcuu uggcaguuuu aaaaaaagga ccagucuuaa cuuauagaaa caauuaucuu    60
aaauuauaaa uuauc                                                    75

<210> SEQ ID NO 26
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 26
ugacaaacca acuaaucaau uaaaaaaaaa uuuuucuaca aagucgauaa aauauuauuu    60
auaagcugau uuaaa                                                    75

<210> SEQ ID NO 27
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 27
uuauaauuua acagaauacg cguuuuauaa aauuuaauau aaaauuauuu aauaguaaac    60
ucaaagauac uuaua                                                    75

<210> SEQ ID NO 28
<211> LENGTH: 75
<212> TYPE: RNA
<213> ORGANISM: Artificial Sequence
<220> FEATURE:
<223> OTHER INFORMATION: Synthetic Constructs

```
<400> SEQUENCE: 28
ugucuuagag uacgauuuua uucuuauuau ucuaucuuau aaaaacagau uuaaaaaacc    60
aauuaauaau cuuua                                                    75

<210> SEQ ID NO 29
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 29
uaagaaaucu cggauugacc ugaaaauaua acaaauaauu aauuauaaca aaaaaucagg    60
aagauaauau uauca                                                    75

<210> SEQ ID NO 30
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 30
aauacuuuua uacuaacuaa cuaaucuuua guucccagaa uuaacuaauu auugaauaua    60
uaaauuuauu uauaa                                                    75

<210> SEQ ID NO 31
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 31
agauaauaac guaauugcua uauuauuaua caauaguaua uaaauauaaa ucauaauau    60 cacgaucuaa aaucc                                                    75

<210> SEQ ID NO 32
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 32
uuuaaaaaua uaaacuuuau uaauuuacug uacugcuaaa uuaaauuuuc aagaaauaua    60
uacuuauaua uuaau                                                    75

<210> SEQ ID NO 33
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 33
aaacaacggg aucuuauaau uaaaaauuaa auuauguug auuaauuuuu gaaacuugau    60
aaguuguuua cuuaa                                                    75
```

```
<210> SEQ ID NO 34
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 34
aaucacguaa uucaacgcua uucaaauuuu aauuuagaau caaaauuuua auaucuauau    60
agaaaauuca gaagu                                                    75

<210> SEQ ID NO 35
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 35
ggagauaccu auugucguu uauauuagua uaaauauuu uuuuuauuug uauuacuaaa      60
auuucaagac uuugu                                                    75

<210> SEQ ID NO 36
<211> LENGTH: 75
<212> TYPE: RNA
<213> ORGANISM: Artificial Sequence
<220> FEATURE:
<223> OTHER INFORMATION: Synthetic Constructs

<400> SEQUENCE: 36
auccuuagcu cgacugaaag aguuuuggau ugauuguuga auauaaaaag uuauuaaauu    60
auaauaauuu ucuua                                                    75

<210> SEQ ID NO 37
<211> LENGTH: 100
<212> TYPE: DNA
<213> ORGANISM: Artificial Sequence
<220> FEATURE:
<223> OTHER INFORMATION: Synthetic Constructs

<400> SEQUENCE: 37
tcaaagtctt cacagttaaa tatacaaaac aagtaaatag tattattaaa caacacacct    60
taaaaataat tctgtaatta attaaaatac aaatagtagg                         100

<210> SEQ ID NO 38
<211> LENGTH: 100
<212> TYPE: DNA
<213> ORGANISM: Artificial Sequence
<220> FEATURE:
<223> OTHER INFORMATION: Synthetic Constructs

<400> SEQUENCE: 38
acgtcttaaa ccagggattt ataagttaaa atcactattt attctataaa ataataacag    60
gtttaaacta atttattaat attaattact actttaagta                         100

<210> SEQ ID NO 39
<211> LENGTH: 100
<212> TYPE: DNA
<213> ORGANISM: Artificial Sequence
<220> FEATURE:
<223> OTHER INFORMATION: Synthetic Constructs
```

```
<400> SEQUENCE: 39
ctcgcctcta tctgttaatt gaattattaa ttatattcac tattttttaa actcttcctc    60
ctttcttctt ttataattaa tataaacgta ataattctat                         100

<210> SEQ ID NO 40
<211> LENGTH: 100
<212> TYPE: DNA
<213> ORGANISM: Artificial Sequence
<220> FEATURE:
<223> OTHER INFORMATION: Synthetic Constructs

<400> SEQUENCE: 40
ttattgtcaa cttgatatct cgtatagcaa tagactatta aaaattttat aagatataat    60
atttaaaatt tattttaata attttaattc ccaaacgtaa                         100

<210> SEQ ID NO 41
<211> LENGTH: 100
<212> TYPE: DNA
<213> ORGANISM: Artificial Sequence
<220> FEATURE:
<223> OTHER INFORMATION: Synthetic Construct

<400> SEQUENCE: 41
atcctagtaa actccaaata cacgacaata tttaaactaa tttaatatta aacttcagaa    60
agggatagta gacaccttct aatagattat ataaaattat                         100
```

METHODS AND VECTORS FOR PRODUCING TRANSGENIC PLANTS

I. CROSS-REFERENCE TO RELATED APPLICATIONS

Figure 1:
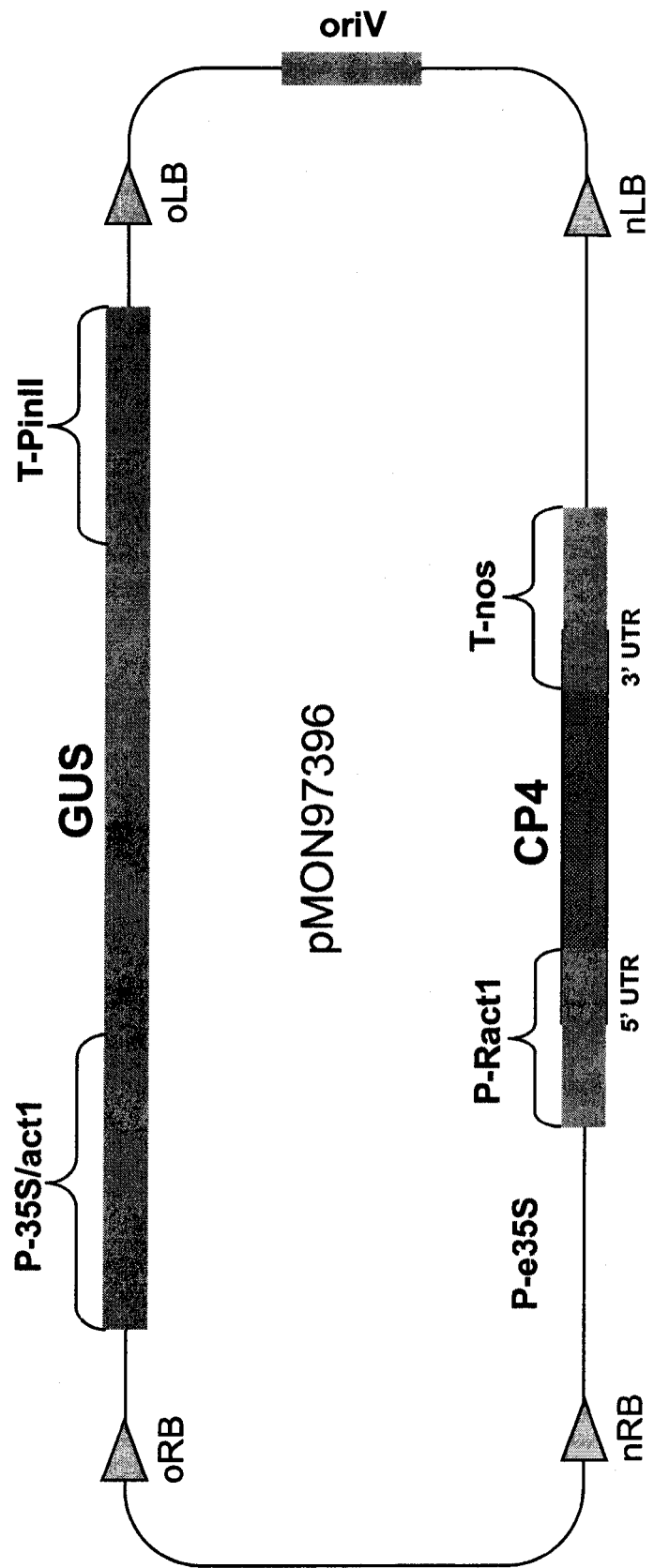

This application claims the benefit under 35 U.S.C. §119(e) of U.S. Provisional Application No. 61/129,739 filed Jul. 16, 2008, which is herein incorporated by reference in its entirety.

II. INCORPORATION OF SEQUENCE LISTING

This application contains an electronic equivalent paper copy of the sequence listing submitted herewith electronically via EFS web and a computer-readable form of the sequence listing submitted herewith electronically via EFS web and contains the file named "SequenceListing.txt", which is 11,330 bytes in size (measured in Windows-XP) and which was created on Jul. 13, 2009.

III. FIELD OF THE INVENTION

Methods of, and compositions for, assembling one or more transcription units in a genome without a linked selectable marker or other unwanted or unnecessary transcription unit are provided. Also provided are methods of, and compositions for, assembling one or more transcription units in a genome with a reduced frequency of vector backbone.

IV. BACKGROUND OF THE INVENTION

Transformation of plant cells by an *Agrobacterium*-mediated method involves exposing plant cells and tissues to a suspension of *Agrobacterium* cells that contain certain DNA plasmids. These plasmids have often been specifically constructed to contain transgenes that will express in plant cells (see, for example, U.S. Pat. No. 5,034,322). Most often, one or more of the transgenes is a selectable marker transgene that permits plant cells to grow in the presence of a positive selection compound, such as an antibiotic or herbicide. These cells can be further manipulated to regenerate into whole fertile plants.

Methods for introducing transgenes into plants by an *Agrobacterium*-mediated transformation method generally involve a T-DNA (transfer DNA) that incorporates the genetic elements of at least one transgene and transfers those genetic elements into the genome of a plant. The transgene(s) are typically constructed in a DNA plasmid vector and are usually flanked by an *Agrobacterium* Ti plasmid right border DNA region (RB) and a left border DNA region (LB). During the process of *Agrobacterium*-mediated transformation, the DNA plasmid is nicked by an endonuclease, VirD2, at the right and left border regions. A single strand of DNA from between the nicks, called the T-strand, is transferred from the *Agrobacterium* cell to the plant cell. The sequence corresponding to the T-DNA region is inserted into the plant genome.

Integration of the T-DNA into the plant genome generally begins at the RB and continues to the end of the T-DNA, at the LB. However, endonucleases sometimes do not nick equally at both borders. When this happens, the T-DNA that is inserted into the plant genome often contains some or all of the plasmid vector DNA. This phenomenon is referred to as "read-through." A desired approach is often that only the transgene(s) located between the right and left border regions (the T-DNA) is transferred into the plant genome without any of the adjacent plasmid vector DNA (the vector backbone). Vector backbone DNA contains various plasmid maintenance elements, including for example, origin of replications, bacterial selectable marker genes, and other DNA fragments that are not required to express the desired trait(s) in plants.

Chen et al. (*Functional Plant Biology* (2005) 32:671-681) assert that they have developed a T-DNA method designed to reduce the frequency of transformed plants with multiple copies of the T-DNA. Chen et al. does not provide a 2T-DNA system and was not designed to specifically eliminate the frequency of transformed plants with linked insertions. Moreover, Chen et al. does not provide a strategy to eliminate vector backbone correlated with linked insertions. The approach of Chen et al. does not permit the transcriptional unit to be oriented in any direction and was not designed to produce single copy plants that are marker-free.

V. BRIEF DESCRIPTION OF FIGURES

FIG. 1: A schematic of a vector pMON97396. Without being limited, pMON97396 has the following elements in order: a right border region, a transcription unit, a left border region, an origin of replication region, a left border region, a transcription unit, a promoter sequence, and a right border region.

Figure 2:
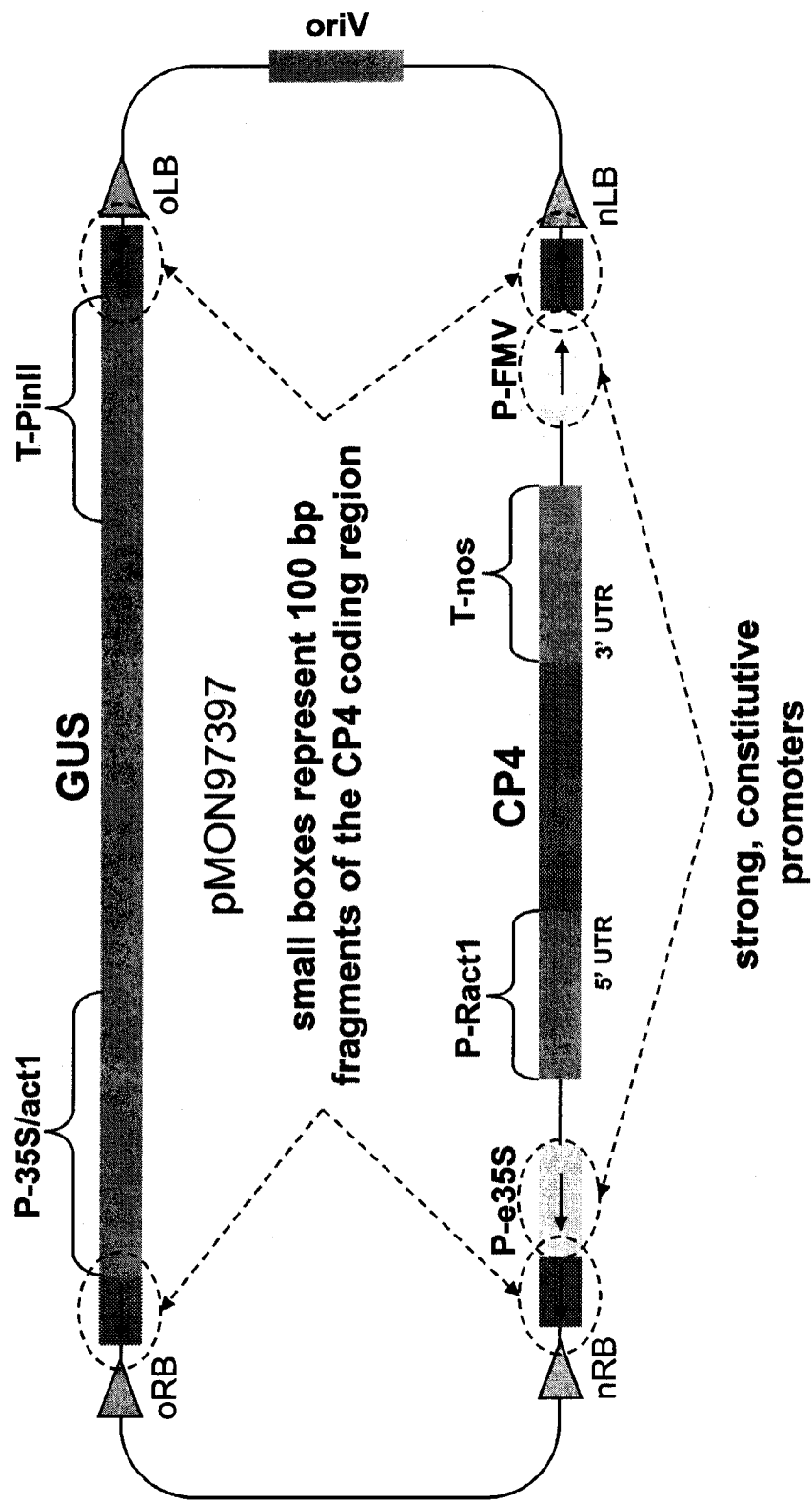

FIG. 2: A schematic of a vector pMON97397. Without being limited, pMON97397 has the following elements in order: a right border region, a shorter transcribable nucleic acid sequence, a transcription unit, a shorter transcribable nucleic acid sequence, a left border region, an origin of replication region, a left border region, a shorter transcribable nucleic acid sequence, a promoter sequence, a transcription unit, a promoter sequence, a shorter transcribable nucleic acid sequence, and a right border region.

Figure 3:
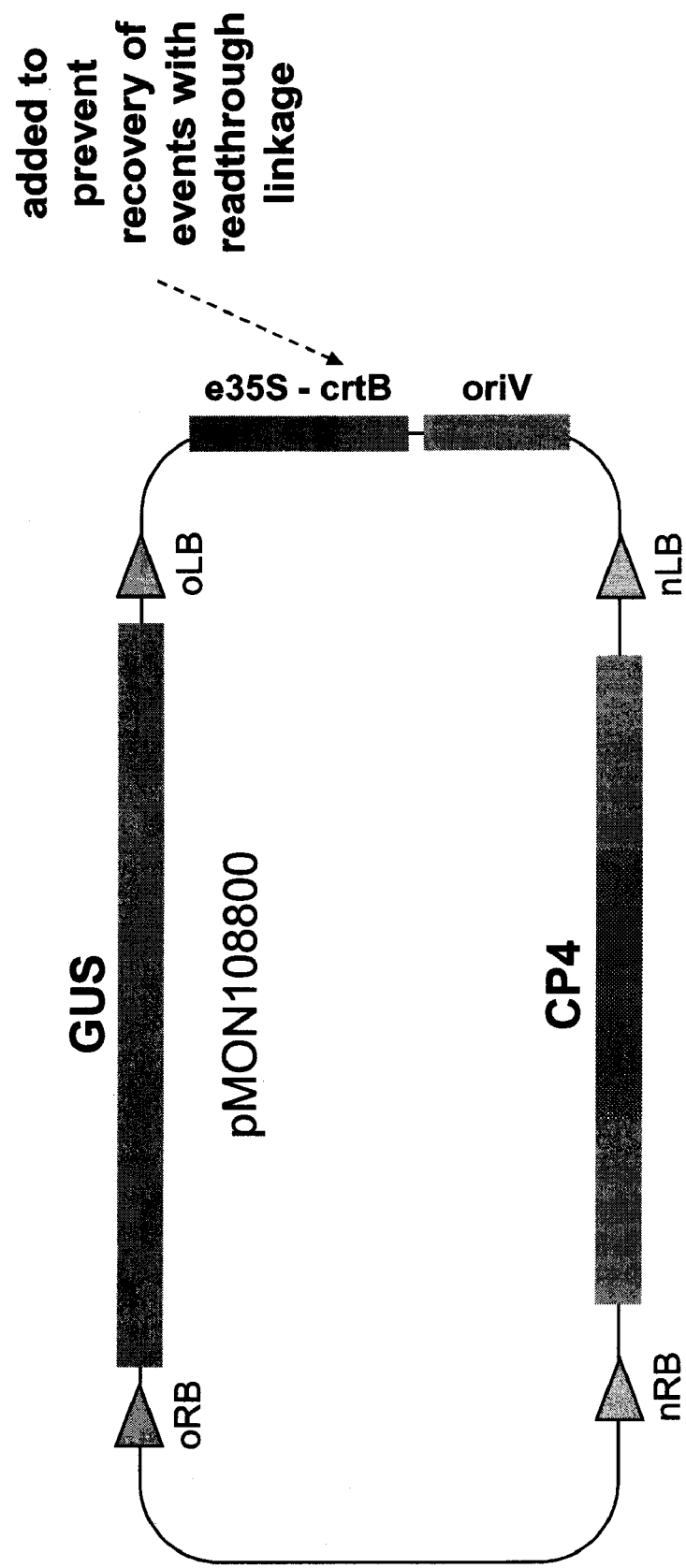

FIG. 3: A schematic of a vector pMON108800. Without being limited, pMON108800 has the following elements in order: a right border region, a transcription unit, a left border region, a non-lethal negative selectable marker gene, an origin of replication, a left border region, a transcription unit, and a right border region.

Figure 4:
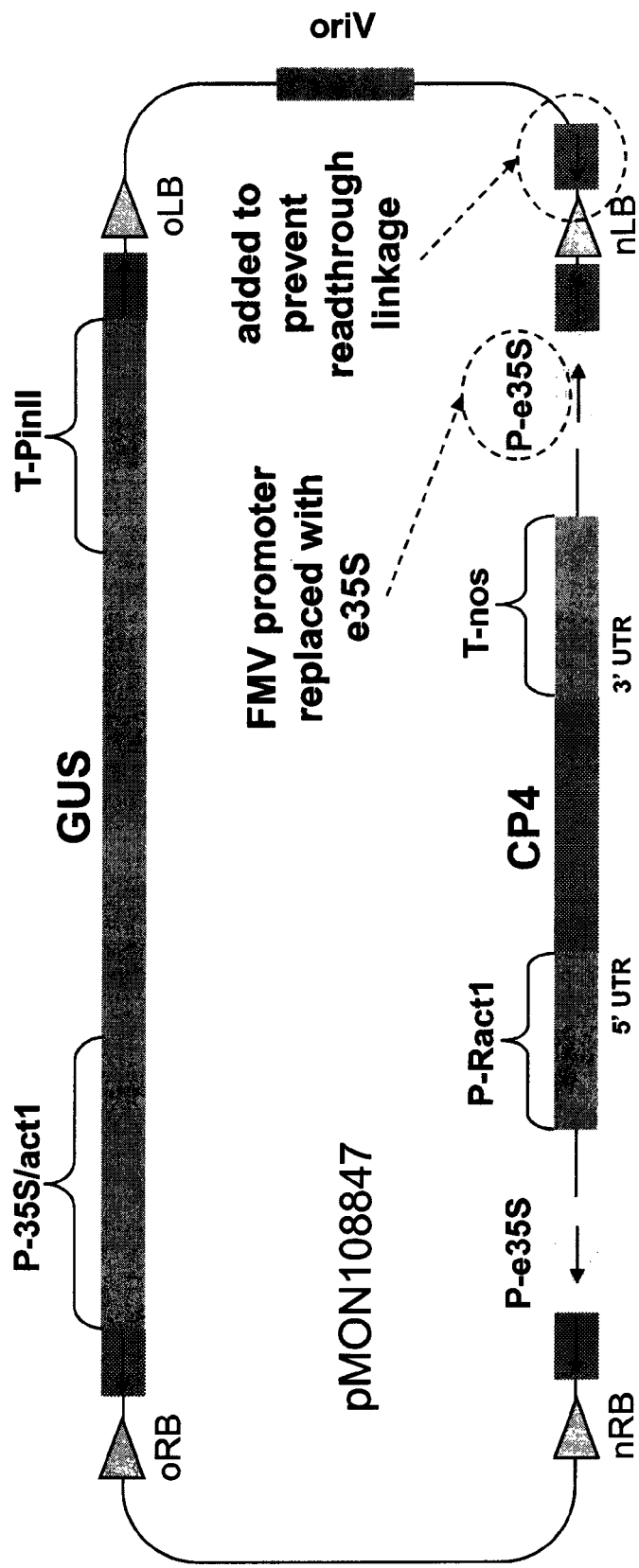

FIG. 4: A schematic of a vector pMON108847. Without being limited, pMON108847 has the following elements in order: a right border region, a shorter transcribable nucleic acid sequence, a transcription unit, a shorter transcribable nucleic acid sequence, a left border region, an origin of replication region, a shorter transcribable nucleic acid sequence, a left border region, a shorter transcribable nucleic acid sequence, a promoter sequence, a transcription unit, a promoter sequence, a shorter transcribable nucleic acid sequence, and a right border region.

Figure 5:
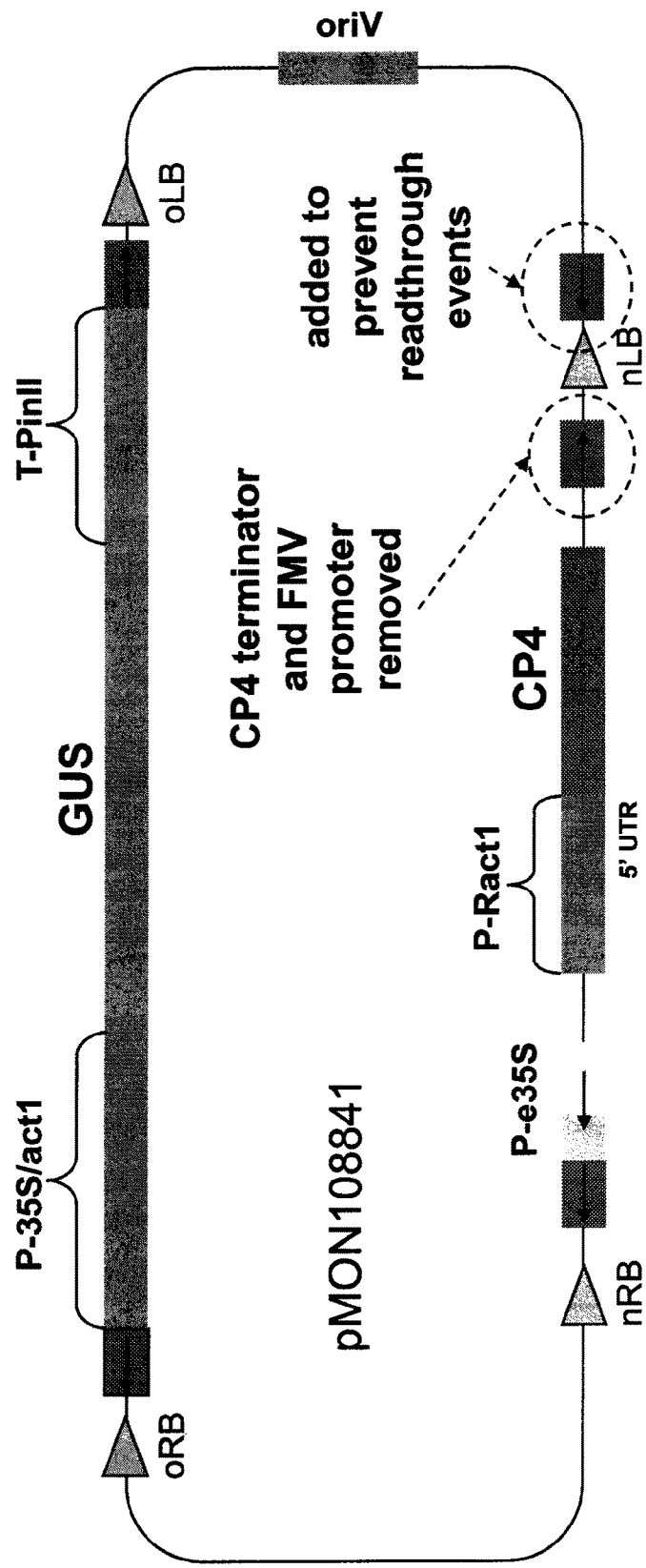

FIG. 5: A schematic of a vector pMON108841. Without being limited, pMON108841 has the following elements in order: a right border region, a shorter transcribable nucleic acid sequence, a transcription unit, a shorter transcribable nucleic acid sequence, a left border region, an origin of replication region, a shorter transcribable nucleic acid sequence, a left border region, a shorter transcribable nucleic acid sequence, a transcription unit, a promoter sequence, a shorter transcribable nucleic acid sequence, and a right border region.

Figure 6:
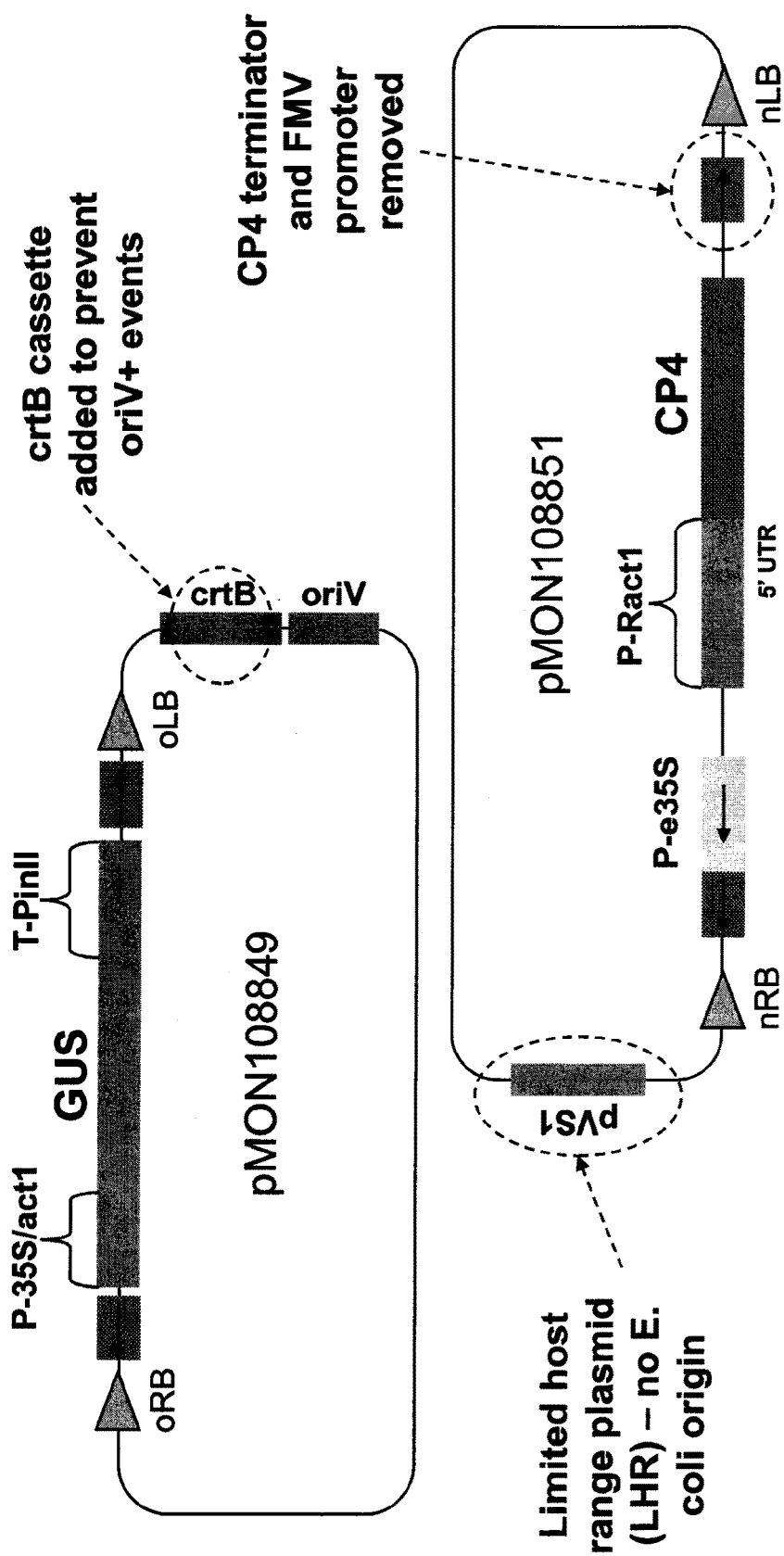

FIG. 6: A schematic of vectors pMON108849 and pMON108851. Without being limited, pMON108849 has the following elements in order: a right border region, a shorter transcribable nucleic acid sequence, a transcription unit, a shorter transcribable nucleic acid sequence, a left border region, a non-lethal negative selectable marker gene, and an origin of replication. Without being limited, pMON108851 has the following elements in order: a Limited Host Range plasmid, a right border region, a shorter transcribable nucleic acid sequence, a promoter, a transcription unit, a shorter transcribable nucleic acid sequence, and a left border region.

Figure 7:
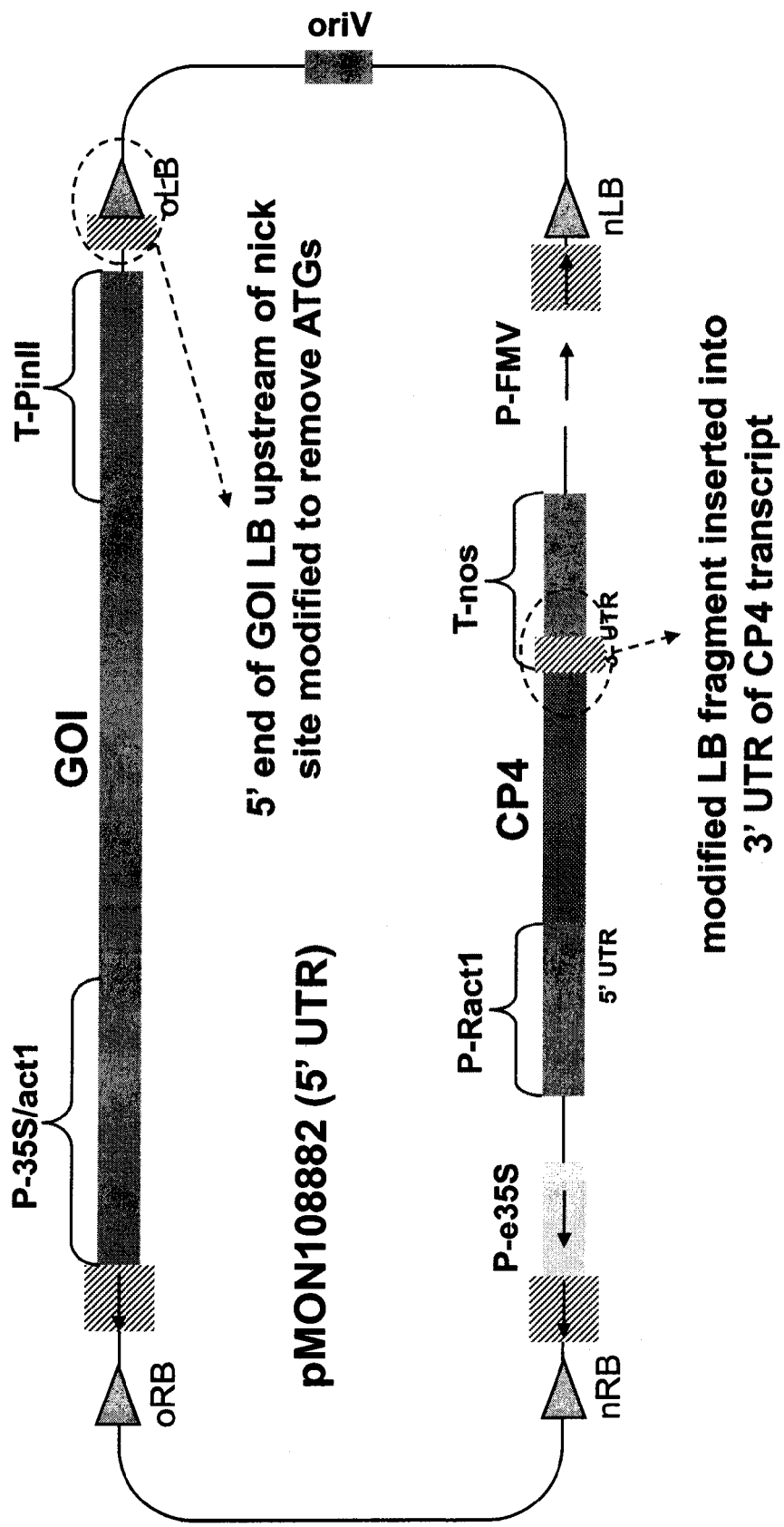

FIG. 7: A schematic of a vector pMON108882. Without being limited, pMON108882 has the following elements in order: a right border region, a shorter transcribable nucleic acid sequence, a transcription unit, a shorter transcribable nucleic acid sequence, a left border region, an origin of replication region, a left border region, a shorter transcribable nucleic acid sequence, a promoter sequence, a transcription unit, a promoter sequence, a shorter transcribable nucleic acid sequence, and a second right border region.

Figure 8:
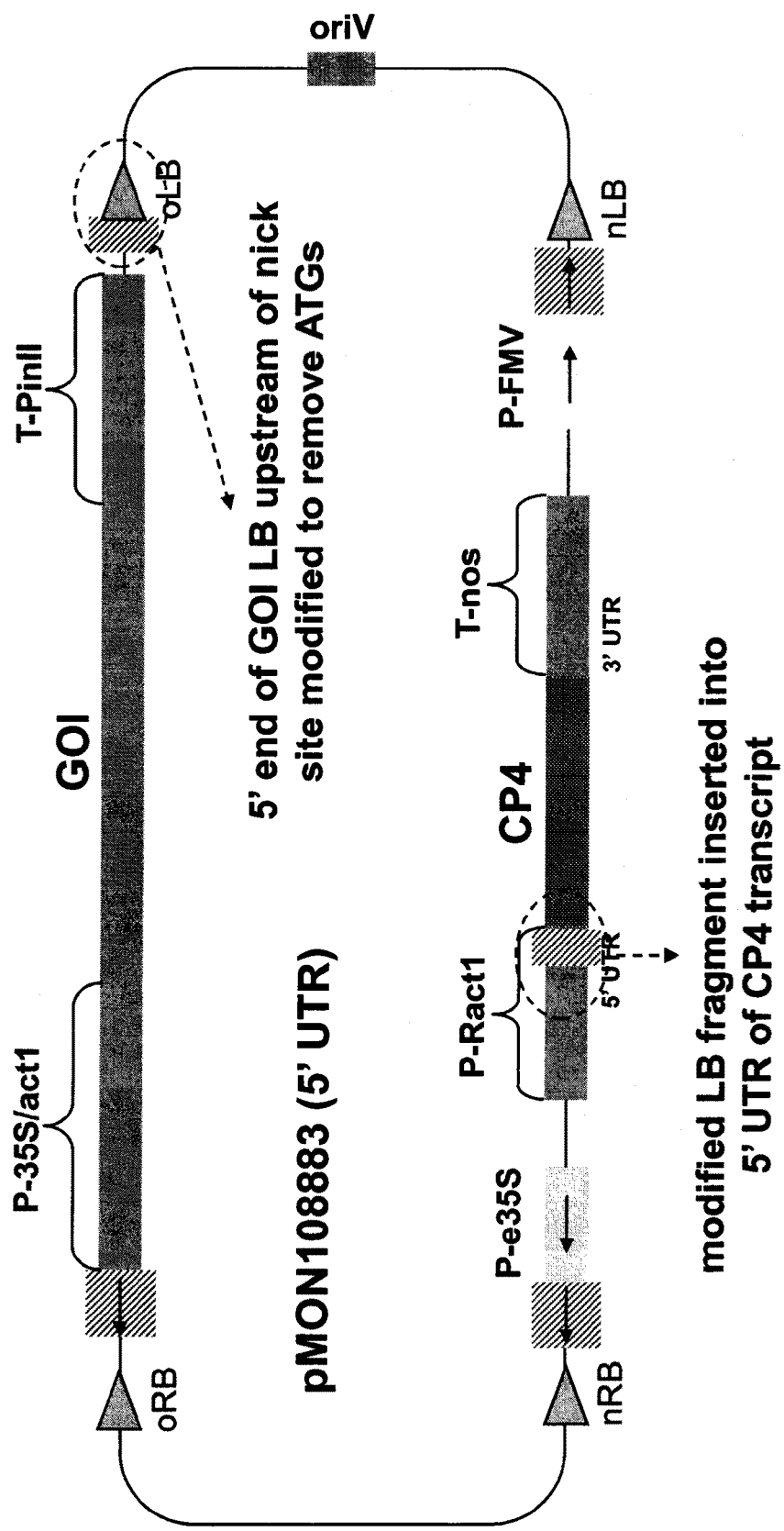

FIG. 8: A schematic of a vector pMON108883. Without being limited, pMON108883 has the following elements in order: a right border region, a shorter transcribable nucleic acid sequence, a transcription unit, a shorter transcribable nucleic acid sequence, a left border region, an origin of replication region, a left border region, a shorter transcribable nucleic acid sequence, a promoter sequence, a transcription unit, a promoter sequence, a shorter transcribable nucleic acid sequence, and a right border region.

Figure 9:
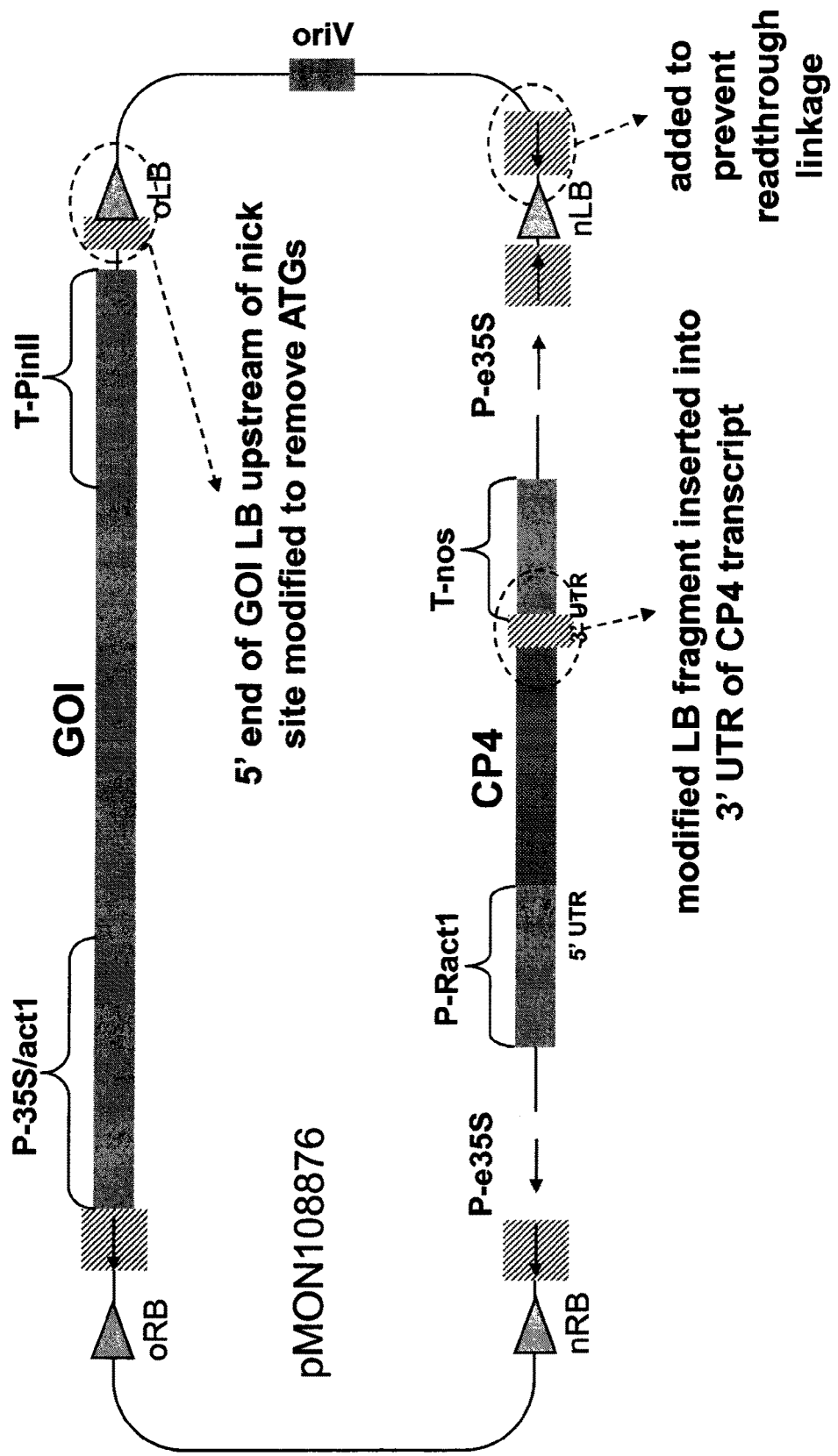

FIG. 9: A schematic of a vector pMON108876. Without being limited, pMON108876 has the following elements in order: a right border region, a shorter transcribable nucleic acid sequence, a transcription unit, a shorter transcribable nucleic acid sequence, a left border region, an origin of replication region, a shorter transcribable nucleic acid sequence, a left border region, a shorter transcribable nucleic acid sequence, a promoter sequence, a transcription unit, a promoter sequence, a shorter transcribable nucleic acid sequence, and a right border region.

Figure 10:
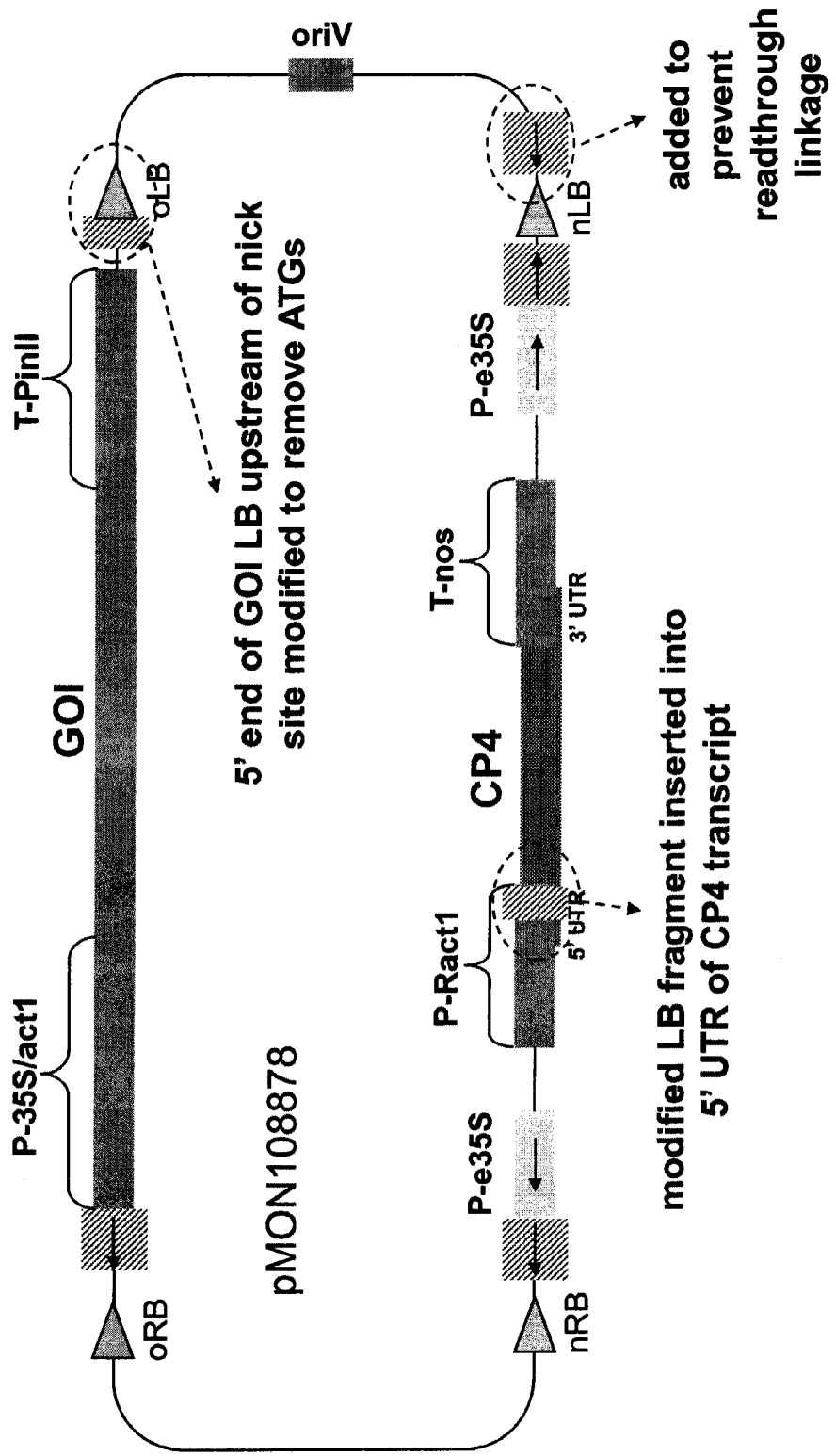

FIG. 10: A schematic of a vector pMON108878. Without being limited, pMON108878 has the following elements in order: a right border region, a shorter transcribable nucleic acid sequence, a transcription unit, a shorter transcribable nucleic acid sequence, a left border region, an origin of replication region, a shorter transcribable nucleic acid sequence, a left border region, a shorter transcribable nucleic acid sequence, a promoter sequence, a transcription unit, a promoter sequence, a shorter transcribable nucleic acid sequence, and a right border region.

Figure 11:
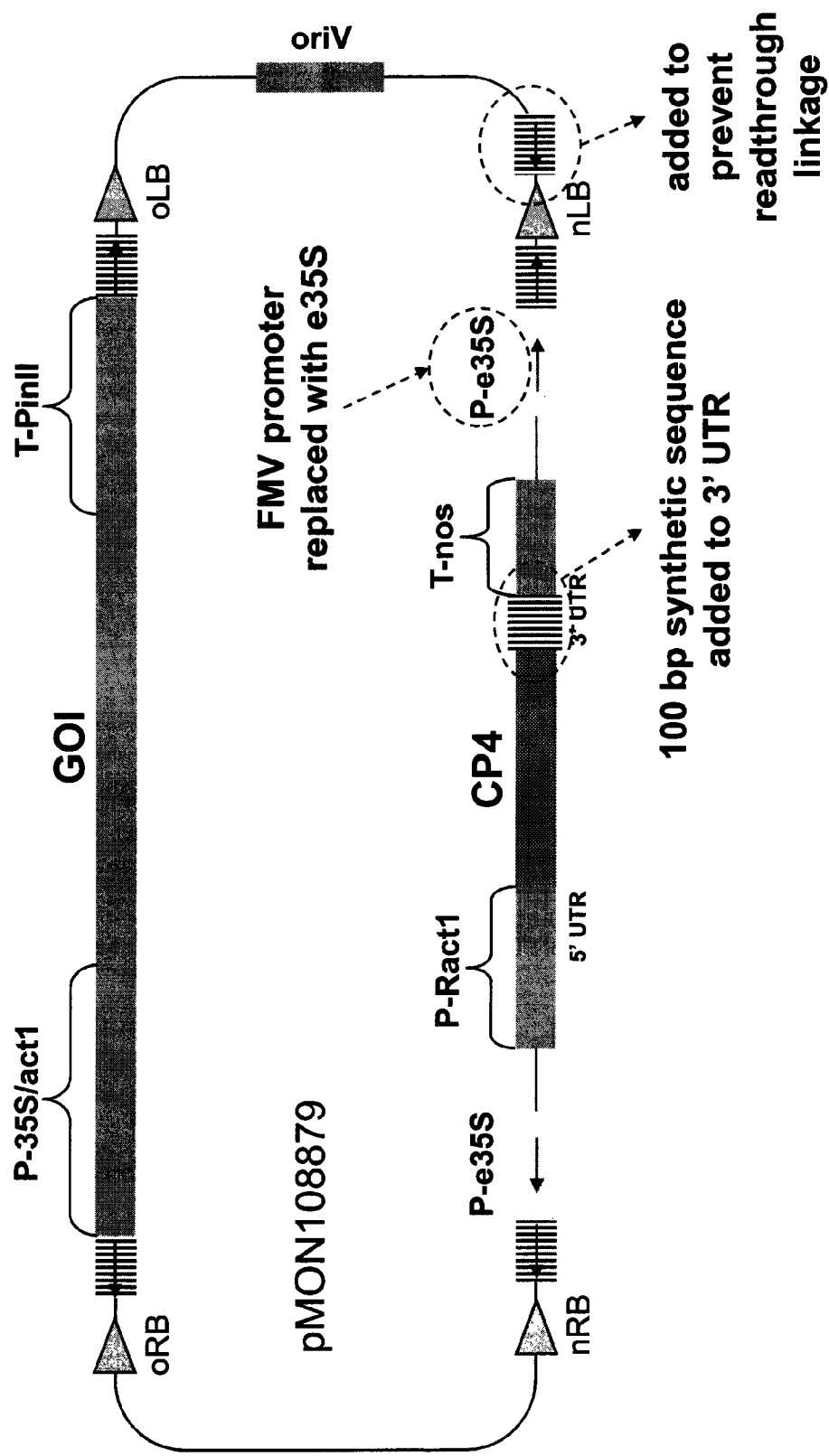

FIG. 11: A schematic of a vector pMON108879. Without being limited, pMON108879 has the following elements in order: a right border region, a shorter transcribable nucleic acid sequence, a transcription unit, a shorter transcribable nucleic acid sequence, a left border region, an origin of replication region, a shorter transcribable nucleic acid sequence, a left border region, a shorter transcribable nucleic acid sequence, a promoter sequence, a transcription unit, a promoter sequence, a shorter transcribable nucleic acid sequence, and a right border region.

Figure 12:
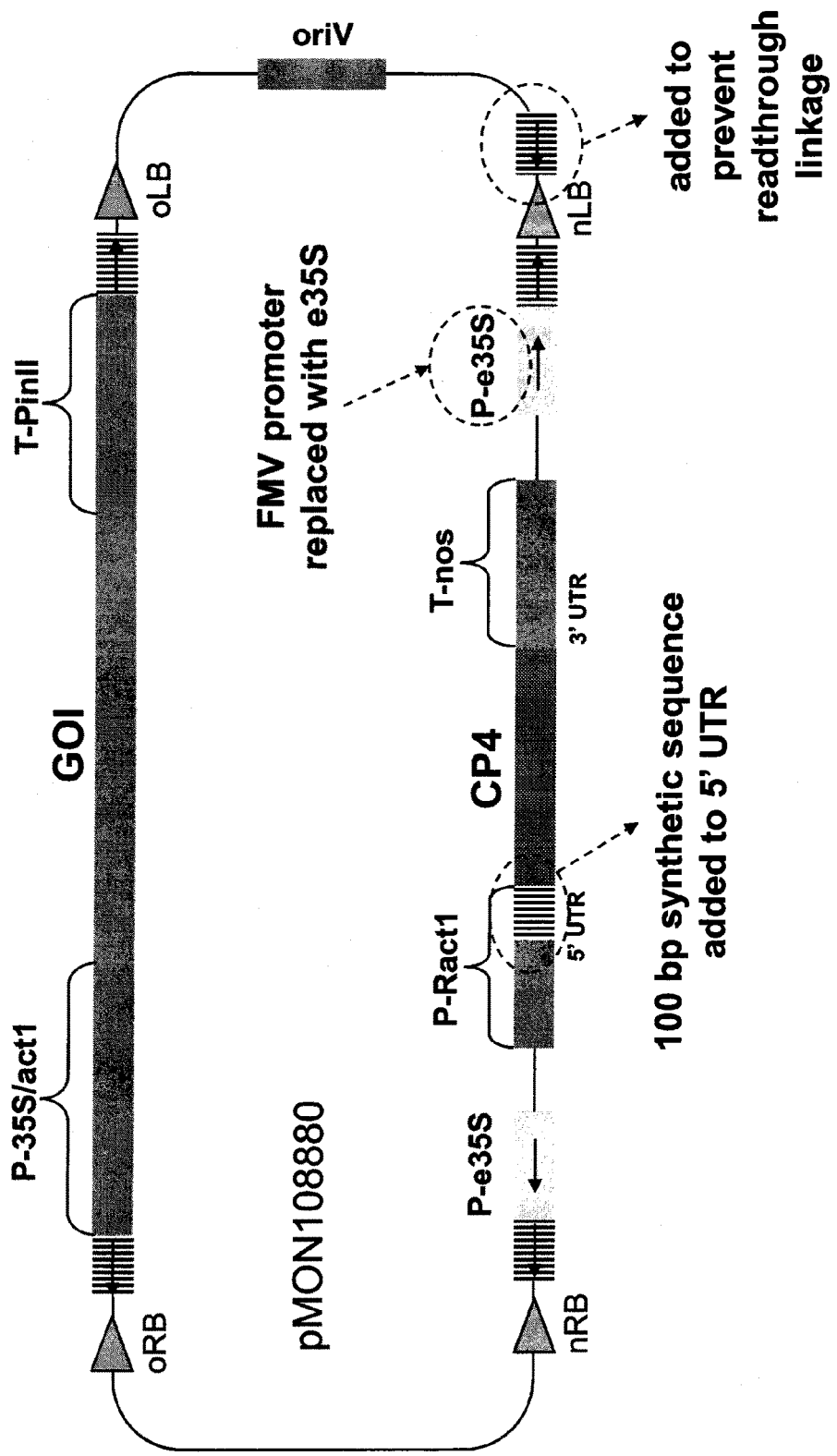

FIG. 12: A schematic of a vector pMON108880. Without being limited, pMON108880 has the following elements: a right border region, a shorter transcribable nucleic acid sequence, a transcription unit, a shorter transcribable nucleic acid sequence, a left border region, an origin of replication region, a shorter transcribable nucleic acid sequence, a left border region, a shorter transcribable nucleic acid sequence, a promoter sequence, a transcription unit, a promoter sequence, a shorter transcribable nucleic acid sequence, and a right border region.

VI. SUMMARY OF THE INVENTION

The present invention includes a nucleic acid molecule comprising a first DNA segment comprising a first transcription unit flanked on both sides by a first and second shorter transcribable nucleic acid sequences in opposite orientation to each other and located between a first left border region and a first right border region, where a first and second transcribable nucleic acid sequences are physically linked to a first border regions and a first border regions flank a first DNA segment; and a second DNA segment comprising a second transcription unit flanked on both sides by a third and fourth shorter transcribable nucleic acid sequence in opposite orientation to each other and located between a second left border region and a second right border region, where a third and fourth shorter transcribable nucleic acid sequences are physically linked to a second border regions and a second border regions flank a second DNA segment, and a third shorter transcribable nucleic acid sequence is physically linked and operably linked to a promoter; where the first, second, third and fourth shorter transcribable nucleic acid sequences are homologous to a portion of a second transcription unit.

The present invention includes a nucleic acid molecule including a DNA segment comprising a transcription unit flanked on both sides by a first and second shorter transcribable nucleic acid sequence in opposite orientation to each other and located between a first left border region and a first right border region, where the first and second shorter transcribable nucleic acid sequences are homologous to a portion of a same or different transcription unit and are physically linked to the first border regions and the first border regions flank the DNA segment. In another aspect, the shorter transcribable nucleic acid sequences are homologous to a portion of a different transcription unit which is a selectable marker gene.

The present invention includes a nucleic acid molecule including a DNA segment comprising a transcription unit flanked on both sides by a first and second shorter transcribable nucleic acid sequence in opposite orientation to each other and located between a first left border region and a first right border region, where the first and second shorter transcribable nucleic acid sequences are homologous to a portion of a same or different transcription unit and are physically linked to the first border regions and the first border regions flank the DNA segment. In another aspect, the shorter transcribable nucleic acid sequences are homologous to a portion of a different transcription unit which is a selectable marker gene.

In another aspect, the present invention includes a nucleic acid molecule including a DNA segment having a transcription unit flanked on both sides by a first and second shorter transcribable nucleic acid sequence in opposite orientation to each other and located between a first left border region and a first right border region, where the first and second shorter transcribable nucleic acid sequences are homologous to a portion of a different transcription unit that contains a selectable marker gene and are physically linked to the first border regions and the first border regions flank the DNA segment. In another aspect, the present invention includes a nucleic acid molecule including a DNA segment with a first transcription unit flanked on both sides by a first and second shorter transcribable nucleic acid sequence in opposite orientation to each other and located between a first left border region and a first right border region, where the first and second shorter transcribable nucleic acid sequences are homologous to a portion of a first or second transcription unit and are physically linked to the first border regions and the first border regions flank the DNA segment, where the first transcription unit does not comprise a termination sequence. In an aspect, the second transcription unit does not comprise a termination sequence. In another aspect, the nucleic acid molecule further has a Limited Host Range (LHR) origin of replication DNA and the shorter transcribable nucleic acid sequences are homologous to a portion of a second transcription unit including a selectable marker.

In another aspect, the present invention includes a nucleic acid molecule including a DNA segment with a first transcription unit flanked on both sides by a first and second shorter transcribable nucleic acid sequence in opposite orientation to each other and located between a first left border region and a first right border region, where the first and second shorter transcribable nucleic acid sequences are homologous to a portion of a second transcription unit and are physically linked to the first border regions and the first border regions flank the DNA segment, and the nucleic acid molecule further has a third transcription unit with a lethal or non-lethal negative selectable marker gene transcription unit located outside of the DNA segment.

The present invention also includes a method of selecting for unlinked first and second transcription units or unlinked first and second DNA segments in a plant cell by introducing a nucleic acid molecule including a first DNA segment including a first transcription unit flanked on both sides by a first shorter transcribable nucleic acid sequence and a second shorter transcribable nucleic acid sequence in opposite orientation to each other and located between a first left border region and a first right border region, where the first and second transcribable nucleic acid sequences are physically linked to the first border regions and the first border regions flank the first DNA segment; and a second DNA segment including a second transcription unit flanked on both sides by a third and fourth shorter transcribable nucleic acid sequence in opposite orientation to each other and located between a second left border region and a second right border region, where the third and fourth shorter transcribable nucleic acid sequences are physically linked to the second border regions and the second border regions flank the second DNA segment, and the third shorter transcribable nucleic acid sequence is physically linked and operably linked to a promoter; where the first, second, third and fourth shorter transcribable nucleic acid sequences are homologous to a portion of the second transcription unit into a plant cell genome; growing the transformed plant cell; and selecting a transgenic plant cell with expression of a sequence of interest within the second transcription unit.

The present invention also includes a method of selecting for unlinked first and second DNA segments in a plant cell by introducing into a plant cell genome a nucleic acid molecule including a first DNA segment including a first transcription unit including a sequence of interest flanked on both sides by a first and a second shorter transcribable nucleic acid sequence in opposite orientation to each other and located between a first left border region and a first right border region, where the first and second shorter transcribable nucleic acid sequences and are physically linked to the first border regions and the first border regions flank the first DNA segment and a second DNA segment including a second transcription unit including a selection marker gene flanked on both sides by a third and fourth shorter transcribable nucleic acid sequence in opposite orientation to each other and located between a second left border region and a second right border region, where the third and fourth shorter transcribable nucleic acid sequences are physically linked to the second border regions and the second border regions flank the second DNA segment, and the third shorter transcribable nucleic acid sequence is physically linked and operably linked to a promoter, and the first, second, third and fourth shorter transcribable nucleic acid sequences are homologous to a portion of the second transcription unit; growing the transformed plant cell; and selecting a transgenic plant cell with expression of the selection marker gene within the second transcription unit.

Also included in the present invention is a method of selecting for linked first and second transcription units or DNA segments in a plant cell by introducing a nucleic acid molecule including a first DNA segment including a first transcription unit flanked on both sides by a first and second shorter transcribable nucleic acid sequences in opposite orientation to each other and located between a first left border region and a first right border region, where the first and second transcribable nucleic acid sequences are physically linked to the first border regions and the first border regions flank the first DNA segment; and a second DNA segment including a second transcription unit flanked on both sides by a third and fourth shorter transcribable nucleic acid sequence in opposite orientation to each other and located between a second left border region and a second right border region, where the third and fourth shorter transcribable nucleic acid sequences are physically linked to the second border regions and the second border regions flank the second DNA segment, and the third shorter transcribable nucleic acid sequence is physically linked and operably linked to a promoter; where the first, second, third and fourth shorter transcribable nucleic acid sequences are homologous to a portion of the second transcription unit into a plant cell genome; growing the transformed plant cell; assaying for expression of a gene within the second transcription unit; and selecting a transgenic cell with limited or no expression of the gene within the second transcription unit.

The present invention also includes a method for producing a transgenic plant capable of expressing a sequence of interest without a selectable marker gene by introducing into a plant cell genome a nucleic acid molecule including a first DNA segment including a first transcription unit including a sequence of interest flanked on both sides by a first and second shorter transcribable nucleic acid sequences in opposite orientation to each other and located between a first left border region and a first right border region, where the first and second transcribable nucleic acid sequences are physically linked to the first border regions and the first border regions flank the first DNA segment; and a second DNA segment including a second transcription unit including a selectable marker gene flanked on both sides by a third and fourth shorter transcribable nucleic acid sequence in opposite orientation to each other and located between a second left border region and a second right border region, where the third and fourth shorter transcribable nucleic acid sequences are physically linked to the second border regions and the second border regions flank the second DNA segment, and the third shorter transcribable nucleic acid sequence is physically linked and operably linked to a promoter; where the first, second, third and fourth shorter transcribable nucleic acid sequences are homologous to a portion of the second transcription unit including a selectable marker gene; growing the transformed plant cell; assaying for expression of the selectable marker gene in the transformed plant cell; selecting a transgenic plant cell with expression of the selectable marker gene; growing a plant from the selected plant cell; selfing said plant expressing said selectable marker gene or crossing the plant expressing the selectable marker with a second plant not expressing a selectable marker; obtaining progeny plant seeds from said selfed or crossed plant; and selecting a progeny plant that does not express a selectable marker and is capable of expressing the gene of interest.

Also included in the present invention includes a method for reducing the frequency of transformed plants with vector backbone sequences by introducing into a plant cell genome a nucleic acid molecule including a first DNA segment including a first transcription unit including a sequence of interest flanked on both sides by a first and second shorter transcribable nucleic acid sequences in opposite orientation to each other and located between a first left border region and a first right border region, where the first and second transcribable nucleic acid sequences are physically linked to the first border regions and the first border regions flank the first DNA segment; and a second DNA segment including a second transcription unit including a selectable marker gene flanked on both sides by a third and fourth shorter transcribable nucleic acid sequence in opposite orientation to each other and located between a second left border region and a second right border region, where the third and fourth shorter transcribable nucleic acid sequences are physically linked to the second border regions and the second border regions flank the second DNA segment, and the third shorter transcribable nucleic acid sequence is physically linked and operably linked to a promoter and the first, second, third and fourth shorter transcribable nucleic acid sequences are homologous to a portion of the second transcription unit; and the nucleic acid molecule including a third transcription unit including a non-lethal negative selectable marker gene located between the first DNA segment and the second DNA segment or growing transformed plant cells; assaying for expression of the selectable marker and healthy growth after transformation; and selecting a healthy, transgenic cell expressing the selectable marker.

Also included in the present invention includes a method for reducing the frequency of transformed plants with vector backbone sequences by introducing into a plant cell genome a nucleic acid molecule including a DNA segment including a transcription unit flanked on both sides by a first and second shorter transcribable nucleic acid sequence in opposite orientation to each other and located between a left border region and a right border region, where the first and second shorter transcribable nucleic acid sequences are physically linked to the border regions and the border regions flank the DNA segment, and the first shorter transcribable nucleic acid sequence is physically linked and operably linked to a promoter and the first and the second shorter transcribable nucleic acid sequences are homologous to a portion of the transcription unit and the nucleic acid molecule including a Limited Host Range (LHR) origin of replication DNA; growing transformed plant cells; assaying for expression of the selectable marker and healthy growth after transformation; and selecting a healthy, transgenic cell expressing the selectable marker.

The present invention includes introducing into a plant cell genome a nucleic acid molecule including a first DNA segment including a first transcription unit and flanked on both sides by a first and second shorter transcribable nucleic acid sequences in opposite orientation to each other and located between a first left border region and a first right border region, where the first and second transcribable nucleic acid sequences are physically linked to the first border regions and the first border regions flank the first DNA segment and a second DNA segment including a second transcription unit and flanked on both sides by a third and fourth shorter transcribable nucleic acid sequence in opposite orientation to each other and located between a second left border region and a second right border region, where the third and fourth shorter transcribable nucleic acid sequences are physically linked to the second border regions and the second border regions flank the second DNA segment, and the third shorter transcribable nucleic acid sequence is physically linked and operably linked to a promoter, and the first, second, third and fourth shorter transcribable nucleic acid sequences are homologous to a portion of the second transcription unit; growing the transformed plant cell; and selecting a transgenic plant cell with expression of a sequence of interest within the second transcription unit.

The present invention also includes introducing into a plant cell genome a nucleic acid molecule including a first DNA segment including a first transcription unit including a sequence of interest and flanked on both sides by a first and second shorter transcribable nucleic acid sequences in opposite orientation to each other and located between a first left border region and a first right border region, where the first and second transcribable nucleic acid sequences are physically linked to the first border regions and the first border regions flank the first DNA segment and a second DNA segment including a second transcription unit including a selection marker gene and flanked on both sides by a third and fourth shorter transcribable nucleic acid sequence in opposite orientation to each other and located between a second left border region and a second right border region, where the third and fourth shorter transcribable nucleic acid sequences are physically linked to the second border regions and the second border regions flank the second DNA segment, and the third shorter transcribable nucleic acid sequence is physically linked and operably linked to a promoter, and the first, second, third and fourth shorter transcribable nucleic acid sequences are homologous to a portion of the second transcription unit; growing the transformed plant cell; and selecting a transgenic plant cell with expression of a selection marker gene within the second transcription unit. In another aspect, the method of the present invention further includes assaying for expression of a sequence of interest within the second transcription unit, such as a selection marker gene.

In an aspect, the present invention includes a method for producing a transgenic plant capable of expressing a sequence of interest without a selectable marker gene by introducing into a plant cell genome a nucleic acid molecule having a first DNA segment with a first transcription unit including a sequence of interest flanked on both sides by a first and second shorter transcribable nucleic acid sequences in opposite orientation to each other and located between a first left border region and a first right border region, where the first and second transcribable nucleic acid sequences are physically linked to the first border regions and the first border regions flank the DNA segment and a second DNA segment with a second transcription unit having a selectable marker gene flanked on both sides by a third and fourth shorter transcribable nucleic acid sequence in opposite orientation to each other and located between a second left border region and a second right border region, where the third and fourth shorter transcribable nucleic acid sequences are physically linked to the second border regions and the second border regions flank the second DNA segment, and the third shorter transcribable nucleic acid sequence is physically linked and operably linked to a promoter where the first, second, third and fourth shorter transcribable nucleic acid sequences are homologous to a portion of the second transcription unit having a selectable marker gene; growing the transformed plant cell; assaying for expression of the selectable marker gene in the transformed plant cell; selecting a transgenic plant cell with expression of the selectable marker gene; growing a plant from the selected plant cell; selfing said plant expressing said selectable marker gene or crossing the plant expressing the selectable marker with a second plant not expressing a selectable marker; obtaining progeny plant seeds from said selfed or crossed plant; and selecting a progeny plant that does not express a selectable marker and is capable of expressing the gene of interest.

In an aspect, the present invention includes a method for reducing the frequency of transformed plants with vector backbone sequences by introducing into a plant cell genome a nucleic acid molecule including a first DNA segment including a first transcription unit including a sequence of interest flanked on both sides by a first and second shorter transcribable nucleic acid sequences in opposite orientation to each other and located between a first left border region and a first right border region, where the first and second transcribable nucleic acid sequences are physically linked to the first border regions and the first border regions flank the first DNA segment; and a second DNA segment including a second transcription unit including a selectable marker gene flanked on both sides by a third and fourth shorter transcribable nucleic acid sequence in opposite orientation to each other and located between a second left border region and a second right border region, where the third and fourth shorter transcribable nucleic acid sequences are physically linked to the second border regions and the second border regions flank the second DNA segment, and the third shorter transcribable nucleic acid sequence is physically linked and operably linked to a promoter and the first, second, third and fourth shorter transcribable nucleic acid sequences are homologous to a portion of the second transcription unit; and the nucleic acid molecule including a third transcription unit including a non-lethal negative selectable marker gene located between the first DNA segment and the second DNA segment; growing transformed plant cells; assaying for expression of the selectable marker and healthy growth after transformation; and selecting a healthy, transgenic cell expressing the selectable marker.

In an aspect, the present invention includes a method for reducing the frequency of transformed plants with vector backbone sequences by introducing into a plant cell genome a nucleic acid molecule including a DNA segment including a transcription unit flanked on both sides by a first and second shorter transcribable nucleic acid sequence in opposite orientation to each other and located between a left border region and a right border region, where the first and second shorter transcribable nucleic acid sequences are physically linked to the border regions and the border regions flank the DNA segment, and the first shorter transcribable nucleic acid sequence is physically linked and operably linked to a promoter and the first and the second shorter transcribable nucleic acid sequences are homologous to a portion of the transcription unit and the nucleic acid molecule including a Limited Host Range (LHR) origin of replication DNA; growing transformed plant cells; assaying for expression of the selectable marker and healthy growth after transformation; and selecting a healthy, transgenic cell expressing the selectable marker.

In an aspect, the present invention includes plant genome including a nucleic acid molecule including a first DNA segment including a first transcription unit flanked on both sides by a first and second shorter transcribable nucleic acid sequences in opposite orientation to each other and located between a first left border region and a first right border region, where the first and second transcribable nucleic acid sequences are physically linked to the first border regions and the first border regions flank the first DNA segment; and a second DNA segment including a second transcription unit flanked on both sides by a third and fourth shorter transcribable nucleic acid sequence in opposite orientation to each other and located between a second left border region and a second right border region, where the third and fourth shorter transcribable nucleic acid sequences are physically linked to the second border regions and the second border regions flank the second DNA segment, and the third shorter transcribable nucleic acid sequence that is homologous to a portion of the second transcription unit is physically linked and operably linked to a promoter; where the first, second, third and fourth shorter transcribable nucleic acid sequences are homologous to a portion of the second transcription unit.

In another aspect, the present invention includes a plant with a plant genome having a nucleic acid molecule including a first DNA segment including a first transcription unit flanked on both sides by a first and second shorter transcribable nucleic acid sequences in opposite orientation to each other and located between a first left border region and a first right border region, where the first and second transcribable nucleic acid sequences are homologous to a portion of a second transcription unit and are physically linked to the first border regions and the first border regions flank the first DNA segment.

In another aspect, the present invention includes a plant with a plant genome having a nucleic acid molecule including a DNA segment including a transcription unit flanked on both sides by a first and second shorter transcribable nucleic acid sequence in opposite orientation to each other and located between a left border region and a right border region, where the first and second shorter transcribable nucleic acid sequences are physically linked to the border regions and the border regions flank the DNA segment, and the first shorter transcribable nucleic acid sequence is physically linked and operably linked to a promoter and the first and the second shorter transcribable nucleic acid sequences are homologous to a portion of the transcription unit.

In another aspect, the present invention includes a plant with a plant genome having a nucleic acid molecule including a first DNA segment including a first transcription unit flanked on both sides by a first and second shorter transcribable nucleic acid sequences in opposite orientation to each other and located between a first left border region and a first right border region, where the first and second transcribable nucleic acid sequences are physically linked to the first border regions and the first border regions flank the first DNA segment not operably linked and not physically linked to a second nucleic acid molecule including a second DNA segment including a transcription unit flanked on both sides by a third and fourth shorter transcribable nucleic acid sequence in opposite orientation to each other and located between a left border region and a right border region, where the third and fourth shorter transcribable nucleic acid sequences are physically linked to the border regions and the border regions flank the DNA segment, and the third shorter transcribable nucleic acid sequence is physically linked and operably linked to a promoter and the first, second, third and fourth shorter transcribable nucleic acid sequences are homologous to a portion of the second transcription unit.

In an aspect, the present invention includes a plant with a plant genome having a nucleic acid molecule including a first DNA segment including a first transcription unit including a sequence of interest flanked on both sides by a first and second shorter transcribable nucleic acid sequences in opposite orientation to each other and located between a first left border region and a first right border region, where the first and second transcribable nucleic acid sequences are physically linked to the first border regions and the first border regions flank the first DNA segment; and a second DNA segment including a second transcription unit including a selectable marker gene flanked on both sides by a third and fourth shorter transcribable nucleic acid sequence in opposite orientation to each other and located between a second left border region and a second right border region, where the third and fourth shorter transcribable nucleic acid sequences are physically linked to the second border regions and the second border regions flank the second DNA segment, and the third shorter transcribable nucleic acid sequence is physically linked and operably linked to a promoter; where the first, second, third and fourth shorter transcribable nucleic acid sequences are homologous to a portion of the second transcription unit.

In another aspect, the present invention includes a plant of the present invention further including a fifth shorter transcribable nucleic acid sequence that is homologous to a portion of the second transcription unit located between the first DNA segment and the second DNA segment and adjacent to the second left border region.

In a preferred aspect, the present invention includes a bacterial cell. In a more preferred aspect, the bacterial cell is competent for the transformation of at least a first plant cell. In a most preferred aspect, the bacterial cell is any one of *Agrobacterium* spp., *Rhizobium* spp., *Sinorhizobium* spp., *Mesorhizobium* spp., *Phyllobacterium* spp., *Ochrobactrum* spp., and *Bradyrhizobium* spp. In a preferred aspect, the present invention includes a plant cell. In a more preferred aspect, the plant cell is a cell from *Acacia*, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, cauliflower, celery, Chinese cabbage, cherry, cilantro, citrus, clementines, coffee, corn, cotton, cucumber, Douglas fir, eggplant, endive, escarole, eucalyptus, fennel, figs, forest trees, gourd, grape, grapefruit, honey dew, jicama, kiwifruit, lettuce, leeks, lemon, lime, Loblolly pine, mango, melon, mushroom, nut, oat, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet corn, sweet potato, sweetgum, tangerine, tea, tobacco, tomato, turf, a vine, watermelon, wheat, yams, and zucchini. In preferred embodiments, the plant is a bean, broccoli, cabbage, canola, carrot, cauliflower, celery, Chinese cabbage, corn, cotton cucumber, eggplant, leek, lettuce, melon, pea, pepper, pumpkin, radish, spinach, soybean, squash, sweet corn, sugarcane, tomato, watermelon, or wheat plant.

In an aspect, the present invention includes a transgenic cell transformed with a nucleic acid molecule including a first DNA segment including a first transcription unit flanked on both sides by a first and second shorter transcribable nucleic acid sequences in opposite orientation to each other and located between a first left border region and a first right border region, where the first and second transcribable nucleic acid sequences are physically linked to the first border regions and the first border regions flank the first DNA segment; and a second DNA segment including a second transcription unit flanked on both sides by a third and fourth shorter transcribable nucleic acid sequence in opposite orientation to each other and located between a second left border region and a second right border region, where the third and fourth shorter transcribable nucleic acid sequences are physically linked to the second border regions and the second border regions flank the second DNA segment, and the third shorter transcribable nucleic acid sequence that is homologous to a portion of the second transcription unit is physically linked and operably linked to a promoter; where the first, second, third and fourth shorter transcribable nucleic acid sequences are homologous to a portion of the second transcription unit.

In an aspect, the present invention includes a transgenic cell transformed with a nucleic acid molecule including a first DNA segment including a first transcription unit flanked on both sides by a first and second shorter transcribable nucleic acid sequences in opposite orientation to each other and located between a first left border region and a first right border region, where the first and second transcribable nucleic acid sequences are homologous to a portion of a second transcription unit and are physically linked to the first border regions and the first border regions flank the first DNA segment.

In an aspect, the present invention includes a cell transformed with a nucleic acid molecule including a DNA segment including a transcription unit flanked on both sides by a first and second shorter transcribable nucleic acid sequence in opposite orientation to each other and located between a left border region and a right border region, where the first and second shorter transcribable nucleic acid sequences are physically linked to the border regions and the border regions flank the DNA segment, and the first shorter transcribable nucleic acid sequence is physically linked and operably linked to a promoter and the first and the second shorter transcribable nucleic acid sequences are homologous to a portion of the transcription unit.

VII. DETAILED DESCRIPTION OF THE INVENTION a. Nucleic Acid Molecules

The present invention includes a nucleic acid molecule including a first DNA segment including a first transcription unit flanked on both sides by a first and a second shorter transcribable nucleic acid sequence, in opposite orientation to each other, located between a first left border region and a first right border region, where a first transcribable nucleic acid sequence and a second transcribable nucleic acid sequence are physically linked to a first left or right border region respectively and the first border regions flank a first DNA segment; and a second DNA segment including a second transcription unit flanked on both sides by a third and a fourth shorter transcribable nucleic acid sequence, in opposite orientation to each other, located between a second left border region and a second right border region, where a third shorter transcribable nucleic acid sequence and a fourth shorter transcribable nucleic acid sequence are physically linked to a second left or right border region and the second border regions flank a second DNA segment, and the third shorter transcribable nucleic acid sequence is physically linked and operably linked to a promoter; where the first, second, third and fourth shorter transcribable nucleic acid sequence are homologous to a portion of a second transcription unit. Several aspects are presented herein, such as FIGS. 2, 4, 5, and 7-12.

In an aspect of the present invention, a DNA segment is any sequence on a DNA molecule capable of being fully inserted into a chromosome. In a preferred aspect, a DNA segment is the nucleic acid sequence between a left and right border region of a T-DNA (See U.S. Pat. Nos. 6,265,638, 5,731,179; U.S. Patent Application Publications US2005/0183170; US2003/110532, herein incorporated by reference) when plant tissue is transformed by *Agrobacterium* or other *Rhizobia*-mediated methods. In one aspect, the DNA segments that can be transferred into a cell may be present on one construct in a bacterial strain being utilized for transformation. In another aspect, the DNA segments can be present on separate constructs in a bacterial strain. In yet another aspect, the DNA segments may be found in separate bacterial cells or strains used together or subsequently for transformation. In yet another aspect, the DNA segments may be found in two separate bacterial cells or strains used together or subsequently for transformation.

In an aspect of the present invention, a transcription unit contains one, or at least one or more, two or more, or at least all of the following: (a) a promoter that functions in a cell to cause the production of a nucleic acid sequence, (b) a sequence of interest, which may be a gene of interest and (c) a 3' non-translated nucleic acid sequence. In a preferred aspect, the 3' non-translated nucleic acid sequence can function in a cell to cause the addition of polyadenylated nucleotides to the 3' end of a structural nucleic acid sequence. The present invention includes a transcription unit that may comprise a termination sequence. In an aspect, an example transcription unit is shown in FIG. 2 as CP4 flanked by P-Ract1 and T-nos. In another aspect, the present invention includes a transcription unit that may not comprise a termination sequence. In an aspect, an example transcription unit is shown in FIG. 5 as CP4 with a P-Ract1 promoter. In an aspect, one or more transcription units do not comprise a termination sequence. In one aspect, the first transcription unit does not share any sequence identity of 21 or more contiguous nucleotides to a shorter transcribable nucleic acid sequence where the shorter transcribable nucleic acid sequence is homologous to a portion of a second, different transcription unit.

One aspect of the present invention includes at least two transcription units, a first and second transcription unit. In an aspect, the first and second transcription units include one or more sequences of interest. A sequence of interest may include a protein coding sequence, a gene element, or a gene of interest (GOI). The gene of interest may or may not be a selectable marker. In a preferred aspect, a sequence of interest is a nucleic acid sequence that is capable of contributing to producing a desirable trait. In an aspect, the sequence of interest can be a nucleic acid sequence that causes the targeted expression or over-expression of an exogenous nucleic acid sequence. In another aspect, the sequence of interest can cause the inhibition of expression of an endogenous gene via gene silencing technologies such as antisense-, co-suppression-mediated mechanisms, RNAi technologies including miRNA (e.g., U.S. Patent Application Publication 2006/0200878).

In a preferred aspect, the present invention also provides for specific nucleic acid molecules including a transcription unit flanked by shorter transcribable nucleic acid sequences. In a preferred aspect, a transcription unit is flanked on both sides by a shorter transcribable nucleic acid sequence such that there is a shorter transcribable nucleic acid sequence upstream and downstream of the transcription unit. In a preferred aspect, one or more shorter transcribable nucleic acid sequences are operably linked, physically linked, or operably and physically linked to a transcription unit. In a more preferred aspect, one shorter transcribable nucleic acid sequence is operably linked, physically linked, or operably and physically linked to a transcription unit and another is not.

In a preferred aspect, a shorter transcribable nucleic acid sequence is a nucleic acid sequence with fewer nucleotides than a first transcription unit or than a second transcription unit. In a preferred aspect, a shorter transcribable nucleic acid sequence is homologous to a portion of a second transcription unit, different than the first transcription unit, and is capable of specifically hybridizing to a second transcription unit or a portion thereof. In this aspect, the first transcription unit does not share any sequence identity of 21 or more contiguous nucleotides to a shorter transcribable nucleic acid sequence. In another aspect, the present invention includes a shorter transcribable nucleic acid sequence that is homologous to a portion of a first transcription unit that has fewer nucleotides than a first transcription unit in length and is capable of specifically hybridizing to first transcription unit or a portion thereof. In a preferred aspect, the first transcription unit includes a selectable marker gene. In another preferred aspect, a shorter transcribable nucleic acid sequence is a nucleic acid sequence with fewer nucleotides than a transcription unit with which the shorter transcribable nucleic acid sequence has sufficiently complementary sequence to be able to form a double stranded RNA structure that can serve as a substrate for enzymes to generate small siRNAs or miRNAs. In another preferred aspect, a shorter transcribable nucleic acid sequence has sufficient sequence identity to a portion of a transcription unit to silence a transcription unit.

A transcription unit may be "essentially silenced" such that the level of a protein or mRNA transcript from the transcription unit having homology to the shorter transcribable nucleic acid sequence is essentially silenced within 90%, preferably 80%, more preferably within 65%, and even more preferably within 50% of the level at which it is found in a cell or organism that lacks a shorter transcribable nucleic acid sequence capable of selectively reducing the transcription unit.

A transcription unit may be "substantially silenced" such that the level of a protein or mRNA transcript from the transcription unit having homology to the shorter transcribable nucleic acid sequence is substantially silenced within 49%, more preferably within 35%, and even more preferably within 24% of the level at which it is found in a cell or organism that lacks a shorter transcribable nucleic acid sequence capable of selectively reducing the transcription unit.

A transcription unit may be "barely silenced" such that the level of a protein or mRNA transcript from the transcription unit having homology to the shorter transcribable nucleic acid sequence is either not altered by a particular event or altered only to an extent that does not affect the physiological function of that protein or mRNA transcript. In a preferred aspect, the level of the agent that is essentially unaffected is within 20%, more preferably within 10%, and even more preferably within 5% of the level at which it is found in a cell or organism that lacks a shorter transcribable nucleic acid sequence capable of selectively reducing the transcription unit.

As used herein, "a selective reduction" of an agent such as a protein or mRNA is relative to a cell or organism lacking a nucleic acid molecule capable of selectively reducing the agent. In a preferred aspect, the level of the agent is selectively reduced by at least 50%, preferably at least more than 75%, and even more preferably by at least more than 90% or 95%.

In a preferred aspect, a shorter transcribable nucleic acid sequence shares greater than 50%, greater than 55%, greater than 60%, greater than 65%, greater than 70%, greater than 80%, greater than 85%, greater than 90%, greater than 95%, greater than 97%, greater than 98%, greater than 99% sequence identity or 100% sequence identity with a second transcription unit or fragment thereof. In a preferred aspect, a second transcription unit is not located on an endogenous chromosome, but is located on a heterologous nucleic acid molecule. In a preferred aspect, a shorter transcribable nucleic acid sequence has at least 21 contiguous nucleotides identical to a second transcription unit. In a preferred aspect, one or more shorter transcribable nucleic acid sequences are identical to any other shorter transcribable nucleic acid sequences. In a preferred aspect, all shorter transcribable nucleic acid sequences are identical.

In a preferred aspect, a shorter transcribable nucleic acid sequence is homologous to a portion of a second transcription unit and is at least 21 nucleotides in length. In this aspect, the first transcription unit does not share any sequence identity of 21 or more contiguous nucleotides to a shorter transcribable nucleic acid sequence. In another aspect, a shorter transcribable nucleic acid sequence is at least 21, 30, 40, 50, 75, 100, or 200 nucleotides in length. In this aspect, the shorter transcribable nucleic acid sequence is not more than 100, 200, 300, 400, 500, or 600 nucleotides in length. In another aspect, a shorter transcribable nucleic acid sequence is between 21 and 200 contiguous residues, 75 and 100 contiguous residues, 50 and 150 contiguous residues, 50 and 300 contiguous residues, or 21 and 500 contiguous residues of a second transcription unit. In a preferred aspect, a shorter transcribable nucleic acid sequence that is homologous to a portion of a second transcription unit has at least 21 contiguous nucleotides identical to a portion of a transcription unit, is identical to the other shorter transcribable nucleic acid sequences and is identical to a transcription unit, where the transcription unit can contain a selectable marker gene.

In a preferred aspect, a shorter transcribable nucleic acid sequence is capable of specifically hybridizing to a first or second transcription unit. For example, shorter transcribable nucleic acid sequences can be capable of hybridizing to a first or second transcription unit, for example, under high or low stringency. In an aspect, shorter transcribable nucleic acid sequences can be substantially homologous sequences to a first or second transcription unit, or a portion thereof. The shorter transcribable nucleic acid sequences can be completely or minimally complementary to a first or second transcription unit, or a portion thereof. In an aspect, the shorter transcribable nucleic acid sequences can be substantially homologous to a first or second transcription unit, or a portion thereof.

In a preferred aspect, a shorter transcribable nucleic acid sequence is not identical to a sequence of interest within a second transcription unit. In this preferred aspect, a shorter transcribable nucleic acid sequence is not identical to a selectable marker gene. In another aspect, a shorter transcribable nucleic acid sequence is a non-natural or synthetic sequence. In a preferred aspect, the non-natural or synthetic sequences have any length that a natural or non-synthetic shorter transcribable nucleic acid sequence can have, at least 19 basepairs (bp), at least 75 bp, or at least 100 bp. In another aspect, a non-natural or synthetic shorter transcribable nucleic acid sequence has a high Reynolds scores, preferably higher than 4, 5, 6, or 7, most preferably higher than 5, lack ATGs (start codons) in both strands, lack putative polyA signals, and lack potential allergenic peptides. In an aspect, a non-natural or synthetic shorter transcribable nucleic acid sequence can have two or more of these features. In an aspect the Reynolds score is determined using a computer program, such as that provided by the siRNA laboratory at Whitehead on the world wide web at jura-wi-mit-edu/bioc/siRNAext. Several such non-natural or synthetic sequences thus identified based on these properties and are disclosed in SEQ ID NOs: 1-36. Additional non-natural or synthetic sequences are disclosed in SEQ IDs: 37-41 and were derived by selecting the 10 best 75 bp sequences from SEQ ID NOs: 1-36 and by combining the first 50 bp from one and the first 50 bp from another into a 100 bp sequence. For example, MTI-5 (87481-50093; SEQ ID NO 41) comprised of the first 50 bp from the synthetic sequence 87481 (SEQ ID NO: 7) followed by the first 50 bp of synthetic sequence 50093 (SEQ ID NO: 8). See Reynolds et al. (2004) *Nat. Biotechnology* 22:326-330, herein incorporated by reference in its entirety. Combined sequences can be checked again to ensure that they still exhibit the above mentioned properties.

A synthetic shorter transcribable nucleic acid sequence can be inserted into a border region, a UTR of a sequence of interest, a UTR of only one sequence of interest, a UTR of two sequences of interest, a UTR of two or more sequences of interest, a UTR of all or any sequences of interest, or more preferably into a UTR of a selectable marker transcription unit. In this aspect, a UTR can be a 5' UTR, a 3' UTR, or both UTRs. A synthetic shorter transcribable nucleic acid sequence can be inserted into a border region and a UTR of a sequence of interest, In a preferred aspect, the synthetic or non-natural sequence or a fragment thereof can be used as a part or entire transcribable nucleic acid sequence so that inverted repeats will form if two or more T-DNAs or DNA segments become linked. The effect of the synthetic sequence on its own on the target gene can be tested by first inserting it in the selectable marker transcription unit and then using a transient transformation assay system to assess its impact on the expression of the selectable marker. In an aspect, a shorter transcribable nucleic acid sequence is homologous to a portion of a transcription unit located in an untranslated region (UTR) of a first or second transcription unit. In an aspect, a shorter transcribable nucleic acid sequence is identical to an untranslated region (UTR) of a second transcription unit, where the UTR can be 5' or 3' to a sequence of interest, more preferably 3' of a selectable marker gene.

In an aspect of the present invention, two shorter transcribable nucleic acid sequences are in opposite orientation to each other such that the sequences read in the 5' to 3' direction as if they were separated by a mirror between the left and right border regions. Phrased differently, read in the 5' to 3' direction, the first nucleotide of the first shorter transcribable nucleic acid sequence is the last nucleotide of the second shorter transcribable nucleic acid sequence and the second nucleotide of the first shorter transcribable nucleic acid sequence is the second to last nucleotide of the second shorter transcribable nucleic acid sequence, etc. In an aspect of the present invention, a shorter transcribable nucleic acid sequence that is homologous to a portion of a second transcription unit is located between border regions such that the 5' end of the sequence homologous to a portion of a second transcription unit is physically closer to the most proximal border region than the 3' end of the sequence homologous to a portion of a second transcription unit. In another aspect, a shorter transcribable nucleic acid sequence that is homologous to a portion of a second transcription unit is located between border regions such that the 3' end of the sequence homologous to a portion of a second transcription unit is physically closer to the most proximal border region than the 5' end of the sequence homologous to a portion of a second transcription unit. In all of the aspects, a border region can be the entire border region or a fragment thereof such that the shorter transcribable nucleic acid sequence is part of the border region. When two shorter transcribable nucleic acid sequences are in opposite orientation to each other, the shorter transcribable nucleic acid sequences can form double-stranded RNA (dsRNA).

In an aspect of the present invention, a nucleic acid molecule has a fifth shorter transcribable nucleic acid sequence located between a first DNA segment and a second DNA segment and physically linked to a second left or right border region, where the fifth shorter transcribable nucleic acid sequence is homologous to a portion of a second transcription unit. Preferably, a fifth shorter transcribable nucleic acid sequence is in the opposite orientation of a first, second, third, or fourth shorter transcribable nucleic acid sequence, which is located within a DNA segment. In an aspect, an example construct is shown in FIG. 5. More preferably, a fifth shorter transcribable nucleic acid sequence is in the opposite orientation of a fourth shorter transcribable nucleic acid sequence, which is located within a second DNA segment. A fifth shorter transcribable nucleic acid sequence is proximal or adjacent to a left or right border region. In a preferred aspect, a fifth shorter transcribable nucleic acid sequence is homologous to a portion of a second transcription unit and is adjacent to a second left border region. In a preferred aspect, a fifth shorter transcribable nucleic acid sequence is homologous to a portion of a second transcription unit and comprises part of a second left border region. In an aspect, an example construct is shown in FIGS. 4, 5, and 9-12.

When two shorter transcribable nucleic acid sequences are in opposite orientation to each other on opposite sides of a border region, the shorter transcribable nucleic acid sequence within the DNA segment is able to form a double-stranded hairpin loop with the shorter transcribable nucleic acid sequence on the other side of the border region, i.e., not located within a DNA segment. Although the compositions are not limited by mechanism of action, it is believed that adding a fifth transcribable nucleic acid sequence would result in a double-stranded RNA hairpin loop forming with another transcribable nucleic acid sequence and a border region if there is readthrough into the vector region of the construct, i.e., beyond the border region. Although the compositions are not limited by mechanism of action, it is believed that this will prevent readthrough linkage by silencing the transcription unit having homology to the shorter transcribable nucleic acid sequence. For example, if the shorter transcribable nucleic acid sequence is homologous to a transcription unit having a selection marker gene, the selection marker will be silenced.

In one aspect, the present invention includes a nucleic acid molecule including a DNA segment including a transcription unit flanked on both sides by a first and second shorter transcribable nucleic acid sequence in opposite orientation to each other and located between a left border region and a right border region, where the first and second shorter transcribable nucleic acid sequences are physically linked to the border regions and the border regions flank the DNA segment, and the first shorter transcribable nucleic acid sequence is physically linked and operably linked to a promoter and the first and the second shorter transcribable nucleic acid sequences are homologous to a portion of said transcription unit, and there is a third shorter transcriptional nucleic acid sequence located outside of the first DNA segment and physically linked to a left or right border region. In another aspect, a third shorter transcribable nucleic acid sequence is adjacent to the left or right border region and in the opposite orientation of a shorter transcribable nucleic acid sequence on the other side of the left or right border region. In an aspect, an example third shorter transcribable nucleic acid is shown in FIGS. 4, 5, and 9-12.

In an aspect of the present invention, a nucleic acid molecule can have a left border region and a right border region. In one aspect, the nucleic acid molecule may be flanked by right, left or right and left border regions or may have no border region. A left or right border region can be of any length such that the DNA segment is capable of transformation of plant tissue performed by *Agrobacterium* or other *Rhizobia*-mediated methods (U.S. Pat. Nos. 6,265,638, 5,731,179; U.S. Patent Application Publications US2005/0183170; 2003110532; US20070271627, herein incorporated by reference in their entirety). In a preferred aspect, a border region is about 455 nucleotides and contains about 25 nucleotide imperfect direct repeats. In a more preferred aspect, the about 455 nucleotides of the border region include a shorter transcribable nucleic acid sequence as described above. In an aspect, an example border region is shown in FIGS. 7-12. In a plasmid for mammalian cell expression, a border region can be any sequence that provides a loop, cleavable or not, for formation of dsRNA.

In an aspect, nucleic acid molecules of the present invention can be used for transformation in the methods of the present invention generally and contain the plasmid backbone DNA segments that provide replication function and antibiotic selection in bacterial cells, for example, an *Escherichia coli* origin of replication such as ori322, a broad host range origin of replication such as oriV or oriRi, and a selectable marker gene. In an aspect, nucleic acid molecules of the present invention further contain a third transcription unit having a lethal or non-lethal negative selectable marker gene located between a first DNA segment and a second DNA segment. A non-lethal negative selectable marker gene can be one of any listed in U.S. Publication No. 2004-0237142, herein incorporated by reference in its entirety, such as GGPP synthases, GA 2-oxidase gene sequences, isopentenyltransferase (IPT), CKI1 (cytokinin-independent 1), ESR-2, ESR1-A, auxin-producing genes, such as indole-3-acetic acid (IAA), iaaM, iaah, roLABC, genes that result in overexpression of ethylene biosynthetic enzymes, VP1 genes, AB13 genes, LEC1 genes, and Bas 1 genes for example. A non-lethal negative selectable marker gene can be included on any plasmid, including the same plasmid as the selectable marker gene. In an aspect, an example non-lethal negative selectable marker gene is shown in FIG. 3. In an aspect, a non-lethal negative selectable marker gene can be included on one vector when doing the 2T-DNA transformation. In an aspect, an example construct is shown in FIG. 6. In a preferred aspect, a non-lethal negative selectable marker gene is a gene resulting in the overexpression of a class of enzymes that use substrates of the gibberellic acid (GA) biosynthetic pathway, but that do not result in the production of bioactive GA. In a more preferred aspect, the non-lethal negative selectable marker gene is a phytoene synthase gene, such as from *Erwinia herbicola* (crtB). In this aspect, a crtB gene is located between a first DNA segment and a second DNA segment.

A nucleic acid sequence may be physically linked to another nucleic acid sequence. As used herein, physically linked means that the physically linked nucleic acid sequences are located on the same nucleic acid molecule, for example a first transcription unit can be physically linked to a second transcription unit as part of a single construct or on the same chromosome. A physical linkage can be adjacent or proximal. A nucleic acid sequence may be adjacent to another nucleic acid sequence. By way of example, a shorter transcribable nucleic acid sequence that is adjacent to a border region has no gap between the shorter transcribable nucleic acid sequence and border region. In such a case, a shorter transcribable nucleic acid sequence is immediately followed or preceded by a border region and there are no nucleotides which do not belong to either the shorter transcribable nucleic acid sequence or border region between the two elements. If a shorter transcribable nucleic acid sequence is adjacent to a border region, at least one of the terminal nucleic acid residues of the shorter transcribable nucleic acid sequence can be chemically bonded to a nucleic acid sequence from a border region.

A nucleic acid sequence may be proximal to another nucleic acid sequence. In an example of a shorter transcribable nucleic acid sequence proximally linked to a border region, nucleotides which are not a part of the shorter transcribable nucleic acid sequence or border region exist between the shorter transcribable nucleic acid sequence and border region. The gap (nucleotide(s) that are not derived from the shorter transcribable nucleic acid sequence or border region) can include for example, without limitation, a stop codon, a restriction site, or an intron, cleavable or not. A gap can be composed of at least approximately three stop codons. A gap can have less than five stop codons in different codon reading frames.

A shorter transcribable nucleic acid sequence can be proximally linked to a border region if a terminal nucleic acid residue of the shorter transcribable nucleic acid sequence is not chemically bonded to a nucleic acid residue from the border region. In a preferred embodiment, if the shorter transcribable nucleic acid sequence is proximally linked to a border region, the last nucleic acid residue of the shorter transcribable nucleic acid sequence can be about 3 residues away from a border region or greater than 5 but less than 20 residues away from a border region. In a preferred aspect, a shorter transcribable nucleic acid sequence can be proximally linked to a border region if the border region can act as a hairpin loop for two complementary RNAs encoded by shorter transcribable nucleic acid sequences. In an aspect, proximal linkage can not be a distance so great as to interfere with a nucleic acid sequence exhibiting its desired function if operably linked.

A nucleic acid sequence may be flanked by another nucleic acid sequence. In a preferred aspect, the present invention also provides for specific nucleic acid molecules including a DNA segment flanked by left and right border regions. In preferred aspect, the left and right border regions are operably linked, physically linked, or operably and physically linked to a DNA segment. In a preferred aspect, a DNA segment is flanked on both sides by left and right border regions such that there is a border region upstream and downstream of the DNA segment.

As used herein, operably linked means that the operably linked nucleic acid sequences exhibit their desired function. A nucleic acid sequence may be operably linked to another nucleic acid sequence. For example, in an aspect of the present invention, a shorter transcribable nucleic acid sequence that is homologous to a portion of the second transcription unit can be operably linked to a promoter on a nucleic acid molecule. When expressed in a cell, an operably linked promoter will transcribe a shorter transcribable nucleic acid sequence into RNA. In another aspect of the present invention, a promoter is operably linked to a first, second, third, fourth, or fifth shorter transcribable nucleic acid sequence that is homologous to a portion of a second or first transcription unit. In another aspect of the present invention, a promoter is operably linked to one or more shorter transcribable nucleic acid sequences. In another aspect of the present invention, a promoter is operably linked to all of the shorter transcribable nucleic acid sequence that is homologous to a portion of the second or first transcription unit.

In another non-limiting example, in an aspect of the present invention, a shorter transcribable nucleic acid sequence can be operably linked to a border region on a nucleic acid molecule. When expressed in a cell, an operably linked shorter transcribable nucleic acid sequence will be transcribed as part of a border region or such that the border region is capable of acting as a hairpin loop in a double-stranded RNA molecule. Moreover, an operably linked shorter transcribable nucleic acid sequence can be part of a border region that is capable of acting as a hairpin loop in a double-stranded RNA molecule. In an aspect of the present invention, a first and/or a second shorter transcribable nucleic acid sequences can be operably linked to a first left or right border region. In an aspect, a third and/or a fourth shorter transcribable nucleic acid sequence can be operably linked to a second border left or right sequence. In another aspect, any or all shorter transcribable nucleic acid sequences can be operably linked to a border region.

In an aspect, a sequence of interest that may be transferred into a plant cell may be present on one transformation vector in a bacterial strain being utilized for transformation. In another aspect, more than one sequence of interest may be present on separate transformation vectors in the same bacterial strain. In yet another aspect, sequences of interest may be found in separate bacterial cells or strains used together for transformation. The present invention includes a nucleic acid molecule including a DNA segment including a transcription unit flanked on both sides by a first and second shorter transcribable nucleic acid sequence in opposite orientation to each other and located between a first left border region and a first right border region, where the first and second shorter transcribable nucleic acid sequences are homologous to a portion of a same or different transcription unit and are physically linked to the first border regions and the first border regions flank the DNA segment. In a preferred aspect, the shorter transcribable nucleic acid sequences are homologous to a portion of a different transcription unit which is a selectable marker gene.

In another aspect, the present invention includes a nucleic acid molecule including a DNA segment having a first transcription unit that does not contain a selection marker gene flanked on both sides by a first and second shorter transcribable nucleic acid sequence in opposite orientation to each other and located between a first left border region and a first right border region, where the first and second shorter transcribable nucleic acid sequences are homologous to a portion of a different transcription unit that contains a selectable marker gene and are physically linked to the first border regions and the first border regions flank the DNA segment. In a preferred aspect, the first transcription unit does not share any sequence identity of 21 or more contiguous nucleotides to a shorter transcribable nucleic acid sequence. In another aspect, the present invention includes a nucleic acid molecule including a DNA segment with a first transcription unit flanked on both sides by a first and second shorter transcribable nucleic acid sequence in opposite orientation to each other and located between a first left border region and a first right border region, where the first and second shorter transcribable nucleic acid sequences are homologous to a portion of a first or second transcription unit and are physically linked to the first border regions and the first border regions flank the DNA segment, where the first transcription unit does not comprise a termination sequence. In an aspect, an example construct is shown in FIG. 6, pMON108851. In an aspect, the second transcription unit does not comprise a termination sequence. In a preferred aspect, the nucleic acid molecule further has a Limited Host Range (LHR) origin of replication DNA and the shorter transcribable nucleic acid sequences are homologous to a portion of a second transcription unit including a selectable marker, e.g. FIG. 6. Examples of such LHR origin of replication DNA include pVS1 (Itoh et al., 1984, Plasmid, 11:206-20; Hajdukiewicz et al., 1994, Plant Mol.

Biol., 1994, 25: 989-94), pSa (Genebank PPU30471; Okumura and Kado, 1992, Gen. Genet. 235: 55-63), oriRi, and repABC replicons (US 20070074314). In a more preferred aspect, the LHR origin of replication DNA is pVS1.

In another aspect, the present invention includes a nucleic acid molecule including a DNA segment with a first transcription unit flanked on both sides by a first and second shorter transcribable nucleic acid sequence in opposite orientation to each other and located between a first left border region and a first right border region, where the first and second shorter transcribable nucleic acid sequences are homologous to a portion of a second transcription unit and are physically linked to the first border regions and the first border regions flank the DNA segment, and the nucleic acid molecule further has a third transcription unit with a non-lethal negative selectable marker gene transcription unit located outside of the DNA segment.

In another aspect, the present invention includes a nucleic acid molecule of the present invention integrated in a genome. In a preferred aspect, a DNA segment of the nucleic acid molecule is a single copy in the genome. In a more preferred aspect, the genome is a plant genome. Various methods have been developed for transferring nucleic acid molecules into plant tissue including high velocity microprojection, microinjection, electroporation, direct DNA uptake and, bacterially-mediated transformation. Bacteria known to mediate plant cell transformation include a number of species of the Rhizobiaceae, including, but not limited to, *Agrobacterium* sp., *Sinorhizobium* sp., *Mesorhizobium* sp., and *Bradyrhizobium* sp. (e.g. Broothaerts et al., 2005; US20050289667; US20050289672; US20070271627). Targets for such transformation have often been undifferentiated tissues, although differentiated tissue also has been used for transient and stable plant transformation, and may be in this instance. Non-limiting examples of these tissues include embryos including immature embryos, callus, cotyledons, hypocotyls, meristems, leaves, stems, or roots.

Reducing the occurrence of linkage between two transcription units in the genome of a cell would increase the efficiency of producing a desirable transgenic cell. Such a transgenic cell would be useful in stacking genes into a commercial product. Genes or nucleic acid sequences are genetically linked if they are so closely associated on a chromosome that they are inherited together in greater than 60%, 70%, 75%, 80%, 85%, or 90% of cases. Linked genes are inherited together at a greater than random rate. For example, if a first and second transcription unit are on separate T-DNAs and inserted into a plant genome as direct or inverted repeats, they are linked. Genes or nucleic acid sequences are physically linked if they are so closely associated on a chromosome that they are inherited together all of the time and have no or little non-vector, e.g., endogenous plant DNA, between them. Little non-vector DNA is defined as comprising 1 to 500 bp or 1 to about 1000 bp of non-vector DNA.

In a preferred embodiment, a second transcription unit can be included in the transformation process to screen, select or otherwise identify cells including a sequence of interest in a first transcription unit. In an aspect of the present invention, the expression or presence of the second transcription unit is undesirable during the process of making a final transgenic product.

A second transcription unit can become undesirable anywhere in the process of making a final transgenic product, for example, in gene stacking. Gene stacking is combining desired traits into one line. One selectable marker can be used repeatedly in gene stacking if the selectable marker is not linked to a first desired trait. For example, a transgenic cell having a first desired trait and a CP4 marker gene can be transformed with a second desired trait using CP4 as the marker gene if the CP4 is removed from the original transgenic cell. In order for the CP4 to be removed from the original transgenic cell, the first desired trait must not be linked to the CP4 marker gene.

In the present invention, a first transcription unit can be physically linked or operably linked to a second transcription unit. If a first transcription unit is physically and operably linked to a second transcription unit, the transcription units can co-segregate.

b. Methods

The present invention includes methods of selecting for unlinked first and second transcription units or DNA segments in a plant cell. The present invention includes introducing into a plant cell genome a nucleic acid molecule including a first DNA segment including a first transcription unit and flanked on both sides by a first and second shorter transcribable nucleic acid sequences in opposite orientation to each other and located between a first left border region and a first right border region, where the first and second transcribable nucleic acid sequences are physically linked to the first border regions and the first border regions flank the first DNA segment and a second DNA segment including a second transcription unit and flanked on both sides by a third and fourth shorter transcribable nucleic acid sequence in opposite orientation to each other and located between a second left border region and a second right border region, where the third and fourth shorter transcribable nucleic acid sequences are physically linked to the second border regions and the second border regions flank the second DNA segment, and the third shorter transcribable nucleic acid sequence is physically linked and operably linked to a promoter, and the first, second, third and fourth shorter transcribable nucleic acid sequences are homologous to a portion of the second transcription unit; growing the transformed plant cell; and selecting a transgenic plant cell with expression of a sequence of interest within the second transcription unit. In a preferred aspect, selecting involves both assaying and identifying at the tissue culture stage. In another preferred aspect, the first transcription unit does not share any sequence identity of 21 or more contiguous nucleotides to a shorter transcribable nucleic acid sequence.

In another preferred aspect, the present invention also includes introducing into a plant cell genome a nucleic acid molecule including a first DNA segment including a first transcription unit including a sequence of interest and flanked on both sides by a first and second shorter transcribable nucleic acid sequences in opposite orientation to each other and located between a first left border region and a first right border region, where the first and second transcribable nucleic acid sequences are physically linked to the first border regions and the first border regions flank the first DNA segment and a second DNA segment including a second transcription unit including a selection marker gene and flanked on both sides by a third and fourth shorter transcribable nucleic acid sequence in opposite orientation to each other and located between a second left border region and a second right border region, where the third and fourth shorter transcribable nucleic acid sequences are physically linked to the second border regions and the second border regions flank the second DNA segment, and the third shorter transcribable nucleic acid sequence is physically linked and operably linked to a promoter, and the first, second, third and fourth shorter transcribable nucleic acid sequences are homologous to a portion of the second transcription unit; growing the transformed plant cell; and selecting a transgenic plant cell with expression of a selection marker gene within the second transcription unit. In a more preferred aspect, the method of the present invention further includes assaying for expression of a sequence of interest within the second transcription unit, such as a selection marker gene.

In an aspect, the present invention includes a method of selecting for unlinked first and second DNA segments in a plant cell by introducing a nucleic acid molecule including a first DNA segment with a first transcription unit located between a first left border region and a first right border region; a second DNA segment with a second transcription unit located between a second left border region and a second right border region; and a third transcription unit including a non-lethal negative selectable marker gene located between a first DNA segment and a second DNA segment; growing a transformed plant cell; and selecting a cell including a first DNA segment and a second DNA segment and lacking the third DNA segment. In one aspect, the first transcription unit includes a sequence of interest. In an aspect, the second transcription unit includes a selectable marker gene. In another aspect, the non-lethal negative selectable marker gene is a phytoene synthase gene.

In an aspect, the present invention includes a method for producing a transgenic plant capable of expressing a sequence of interest without a selectable marker gene by introducing into a plant cell genome a nucleic acid molecule including a first DNA segment with a first transcription unit including a sequence of interest flanked on both sides by a first and second shorter transcribable nucleic acid sequences in opposite orientation to each other and located between a first left border region and a first right border region, where the first and second shorter transcribable nucleic acid sequences are physically linked to the first border regions and the first border regions flank the first DNA segment and the nucleic acid molecule further including a second DNA segment with a second transcription unit having a selectable marker gene flanked on both sides by a third and fourth shorter transcribable nucleic acid sequence in opposite orientation to each other and located between a second left border region and a second right border region, where the third and fourth shorter transcribable nucleic acid sequences are physically linked to the second border regions and the second border regions flank the second DNA segment, and the third shorter transcribable nucleic acid sequence is physically linked and operably linked to a promoter where the first, second, third and fourth shorter transcribable nucleic acid sequences are homologous to a portion of the second transcription unit having a selectable marker gene; growing the transformed plant cell; assaying for expression of the selectable marker gene in the transformed plant cell; selecting a transgenic plant cell with expression of the selectable marker gene; growing a plant from the selected plant cell; selfing the plant expressing said selectable marker gene or crossing the plant expressing the selectable marker with a second plant not expressing a selectable marker; obtaining progeny plant seeds from the selfed or crossed plant; and selecting a progeny plant that does not express a selectable marker and is capable of expressing the gene of interest. In this aspect, the nucleic acid molecule can further include a Limited Host Range (LHR) origin of replication DNA located outside of either DNA segment. In another aspect, the nucleic acid molecule can also include a fifth shorter transcribable nucleic acid sequence homologous to a portion of the second transcription unit located outside of either DNA segment and can include a third transcription unit with a non-lethal negative selectable marker gene located outside of either DNA segment.

In another aspect, the present invention includes a method for producing a transgenic plant capable of expressing a sequence of interest without a selectable marker gene by introducing into a plant cell genome a first nucleic acid molecule including a first DNA segment with a first transcription unit including a sequence of interest flanked on both sides by a first and second shorter transcribable nucleic acid sequences in opposite orientation to each other and located between a first left border region and a first right border region, where the first and second shorter transcribable nucleic acid sequences are physically linked to the first border regions and the first border regions flank the first DNA segment and a second nucleic acid molecule including a second DNA segment with a second transcription unit having a selectable marker gene flanked on both sides by a third and fourth shorter transcribable nucleic acid sequence in opposite orientation to each other and located between a second left border region and a second right border region, where the third and fourth shorter transcribable nucleic acid sequences are physically linked to the second border regions and the second border regions flank the second DNA segment, and the third shorter transcribable nucleic acid sequence is physically linked and operably linked to a promoter where the first, second, third and fourth shorter transcribable nucleic acid sequences are homologous to a portion of the second transcription unit having a selectable marker gene; growing the transformed plant cell; assaying for expression of the selectable marker gene in the transformed plant cell; selecting a transgenic plant cell with expression of the selectable marker gene; growing a plant from the selected plant cell; selfing the plant expressing said selectable marker gene or crossing the plant expressing the selectable marker with a second plant not expressing a selectable marker; obtaining progeny plant seeds from the selfed or crossed plant; and selecting a progeny plant that does not express a selectable marker and is capable of expressing the gene of interest. In this aspect, the second nucleic acid molecule can further include a Limited Host Range (LHR) origin of replication DNA located outside of the second DNA segment. In another aspect, the second nucleic acid molecule also can include a fifth shorter transcribable nucleic acid sequence homologous to a portion of the second transcription unit located outside of the second DNA segment and adjacent to the second left border region. Either the first or second nucleic acid molecule can include a third transcription unit with a non-lethal negative selectable marker gene located outside of a DNA segment.

In an aspect, the present invention includes a method for reducing the frequency of transformed plants with vector backbone sequences by introducing into a plant cell genome a nucleic acid molecule including a first DNA segment including a first transcription unit including a sequence of interest flanked on both sides by a first and second shorter transcribable nucleic acid sequences in opposite orientation to each other and located between a first left border region and a first right border region, where the first and second transcribable nucleic acid sequences are physically linked to the first border regions and the first border regions flank the first DNA segment; and a second DNA segment including a second transcription unit including a selectable marker gene flanked on both sides by a third and fourth shorter transcribable nucleic acid sequence in opposite orientation to each other and located between a second left border region and a second right border region, where the third and fourth shorter transcribable nucleic acid sequences are physically linked to the second border regions and the second border regions flank the second DNA segment, and the third shorter transcribable nucleic acid sequence is physically linked and operably linked to a promoter and the first, second, third and fourth shorter transcribable nucleic acid sequences are homologous to a portion of the second transcription unit; and the nucleic acid molecule including a third transcription unit including a non-lethal negative selectable marker gene located between the first DNA segment and the second DNA segment; growing transformed plant cells; assaying for expression of the selectable marker and healthy growth after transformation; and selecting a healthy, transgenic cell expressing the selectable marker. In one aspect, the present invention includes a method for reducing the frequency of transformed plants with vector backbone sequences, introducing a nucleic acid molecule including a third shorter transcribable nucleic acid sequence that is homologous to a portion of a transcription unit and not located within a DNA segment and adjacent to a left border region.

The present invention provides significantly reducing the frequency of cells transformed with vector backbone DNA. Vector backbone DNA is the nucleic acid sequences that are not part of a DNA segment including a sequence of interest. In an aspect, the frequency of cells transformed without vector backbone DNA is more than or equal to about 60%, about 70%, or about 80% of transformed recovered cells. In some embodiments, the frequency of cells transformed without vector backbone DNA as compared to those with vector backbone is more than or equal to about 85%, or more than equal to about 90%, or more than or equal to about 98% or 99%.

Methods of the invention yield an increase in one- or two-copy transformation events. In an aspect, methods of the invention yield a statistically significant increase in one- or two-copy transformation events as compared to similar methods using a conventional vector having two sets of LB/RB flanking two transcription units, such as pMON97396 disclosed in FIG. 1. In an aspect, the frequency of one- or two-copy transformation events is about 30%, about 40%, about 50%, about 60%, about 70%, about 80% of transformations attempted, as measured using DNA detection technologies, such as Southern blotting or PCR. In an aspect, the frequency of one- or two-copy transformation events is about 60% to 55%, 70% to 65%, 70% to 50%, 70% to 60% or 60% to 50% of transformations attempted, as measured using Southern blotting. In an aspect, the frequency of one-copy transformation events out of all attempts is about 1.5 times more or 1.5-3 times more compared to cells without a nucleic acid of the present invention, such as pMON87488, as measured with TaqMan® assay (Applied Biosystems, Foster City, Calif.). It is easier to identify an event with an unlinked gene of interest (GOI) at $R_0$ generation and a marker-free homozygous event at $R_1$ generation if there are a high percentage of one- or two-copy transformation events. One- or two-copy events have lower complexity of T-DNA insertions and are therefore of commercial value.

In an aspect, use of a nucleic acid of the present invention in the transformation of a cell increases the number of cells having the first transcriptional unit unlinked from the second transcriptional unit. In a preferred aspect, use of a nucleic acid of the present invention in the transformation of a cell increases the number of cells having unlinked first and second transcriptional units when there is an increase in one- or two-copy transformation events. In a preferred aspect, the unlinked transcription units contain a sequence of interest unlinked from a selectable marker gene. In an aspect, the number of recovered transformation events yielding two unlinked transcription units is about 0.5% more, about 1% more, about 1.5% more, about 2% more, about 2.5% more, about 3% more, about 5% more, about 10% more, about 20% more, about 30% more, about 40% more, or about 50% more when using a nucleic acid molecule or method of the present invention than when using a conventional vector having two sets of LB/RB flanking two transcription units, such as pMON97396. The frequency of unlinked or linked first and second segments can be determined by methods such as those described in PCT publication WO2009055597, which is herein incorporated by reference in its entirety. The frequency of unlinked or linked first and second segments can also be determined by Southern blot analysis.

In an aspect, the present invention includes a method for reducing the frequency of transformed plants with vector backbone sequences relative to a conventional vector having two sets of LB/RB flanking two transcription units, such as pMON97396 which lacks shorter transcribable nucleic acid sequences, by introducing into a plant cell genome a first nucleic acid molecule including a first DNA segment including a first transcription unit including a sequence of interest that is not a selectable marker flanked on both sides by a first and a second shorter transcribable nucleic acid sequence in opposite orientation to each other and located between a first left border region and a right border region, where the first and second shorter transcribable nucleic acid sequences are physically linked to the first border regions and the first border regions flank the DNA segment, and the first shorter transcribable nucleic acid sequence is physically linked and operably linked to a promoter and the first nucleic acid molecule further includes a second transcription unit having a lethal or non-lethal negative selectable marker gene located outside of the first DNA segment and a second nucleic acid molecule including a second DNA segment including a third transcription unit including a selectable marker gene flanked on both sides by a third and fourth shorter transcribable nucleic acid sequence in opposite orientation to each other and located between a second left border region and a second right border region, where the third and fourth shorter transcribable nucleic acid sequences are physically linked to the second border regions and the second border regions flank the second DNA segment, and the third shorter transcribable nucleic acid sequence is physically linked and operably linked to a promoter and the first, second, third and fourth shorter transcribable nucleic acid sequences are homologous to a portion of the third transcription unit; and the second nucleic acid molecule further includes a Limited Host Range (LHR) origin of replication DNA located outside of the second DNA segment and the first, second, third, and fourth shorter transcribable nucleic acid sequences are homologous to a portion of the third transcription unit; growing transformed plant cells; assaying for expression of the selectable marker and healthy growth after transformation; and selecting a healthy, transgenic cell expressing the selectable marker. In a preferred aspect, the second nucleic acid molecule also includes a fifth shorter transcribable nucleic acid sequence homologous to a portion of the third transcription unit located outside of the second DNA segment and adjacent to the second left border region.

c. Genome

In an aspect, the present invention includes a nucleic acid molecule of the present invention within a genome. In a preferred aspect, the genome is the nuclear genome of a plant cell. Included in the present invention are linked and unlinked versions of the nucleic acid molecules of the present invention. A genome of the present invention includes two or more DNA segments of the present invention inserted into the genome as inverted or direct repeats. In a preferred aspect, a genome of the present invention includes a single copy of a first DNA segment of the present invention not linked to a second DNA segment of the present invention. In another preferred aspect, the present invention includes a genome lacking a selectable marker gene.

In an aspect, the present invention includes a plant genome including a nucleic acid molecule including a first DNA segment including a first transcription unit flanked on both sides by a first and a second shorter transcribable nucleic acid sequences in opposite orientation to each other and located between a first left border region and a first right border region, where the first and second transcribable nucleic acid sequences are physically linked to the first border regions and the first border regions flank the first DNA segment; and a second DNA segment including a second transcription unit flanked on both sides by a third and fourth shorter transcribable nucleic acid sequence in opposite orientation to each other and located between a second left border region and a second right border region, where the third and fourth shorter transcribable nucleic acid sequences are physically linked to the second border regions and the second border regions flank the second DNA segment, and the third shorter transcribable nucleic acid sequence that is homologous to a portion of the second transcription unit is physically linked and operably linked to a promoter; where the first, second, third and fourth shorter transcribable nucleic acid sequences are homologous to a portion of the second transcription unit. In an aspect, an example construct is shown in FIG. 4. In another aspect, the nucleic acid molecule also includes a fifth shorter transcribable nucleic acid sequence homologous to a portion of the second transcription unit located outside of a DNA segment and adjacent to the second left border region. In an aspect, example constructs are shown in FIGS. 4-5. This genome can also include a third transcription unit with a non-lethal negative selectable marker gene located outside of a DNA segment. The present invention includes a transcription unit that may comprise a termination sequence. In an aspect, an example construct is shown in FIG. 2. In another aspect, the present invention includes a transcription unit that may not comprise a termination sequence. In an aspect, an example construct is shown in FIG. 5. In one aspect, a transcription unit does not comprise a termination sequence. In an aspect, the second transcription unit does not comprise a termination sequence.

In a preferred aspect, the present invention includes a plant genome including a nucleic acid molecule including a first DNA segment including a first transcription unit flanked on both sides by a first and second shorter transcribable nucleic acid sequences in opposite orientation to each other and located between a first left border region and a first right border region, where the first and second transcribable nucleic acid sequences are homologous to a portion of a second transcription unit and are physically linked to the first border regions and the first border regions flank the first DNA segment.

In a preferred aspect, the present invention includes a plant with a plant genome having a nucleic acid molecule including a DNA segment including a transcription unit flanked on both sides by a first and second shorter transcribable nucleic acid sequence in opposite orientation to each other and located between a left border region and a right border region, where the first and second shorter transcribable nucleic acid sequences are physically linked to the border regions and the border regions flank the DNA segment, and the first shorter transcribable nucleic acid sequence is physically linked and operably linked to a promoter and the first and the second shorter transcribable nucleic acid sequences are homologous to a portion of the same or a different transcription unit. In a preferred aspect, the first and the second shorter transcribable nucleic acid sequences are homologous to a portion to a different transcription unit, such as an unwanted transcription unit that is or is not in the same genome. The unwanted transcription unit may be unwanted as a result of another sequence within the same T-DNA, such as splA. In another aspect, the plant genome also includes a third shorter transcribable nucleic acid sequence homologous to a portion of the same or a different transcription unit located outside of the DNA segment and adjacent to the left or right border, preferably the left border region. This genome can also include a third transcription unit with a non-lethal negative selectable marker gene located outside of a DNA segment.

In another aspect, the present invention includes a plant with a plant genome having a first DNA segment including a first transcription unit flanked on both sides by a first and second shorter transcribable nucleic acid sequences in opposite orientation to each other and located between a first left border region and a first right border region, where the first and second transcribable nucleic acid sequences are physically linked to the first border regions and the first border regions flank the first DNA segment not operably linked and not physically linked to a second DNA segment including a transcription unit flanked on both sides by a third and fourth shorter transcribable nucleic acid sequence in opposite orientation to each other and located between a left border region and a right border region, where the third and fourth shorter transcribable nucleic acid sequences are physically linked to the border regions and the border regions flank the DNA segment, and the third shorter transcribable nucleic acid sequence is physically linked and operably linked to a promoter and the first, second, third and fourth shorter transcribable nucleic acid sequences are homologous to a portion of the second transcription unit. In a preferred aspect, the first transcription unit includes a sequence of interest without a selectable marker gene and the second transcription unit includes a selectable marker. In an aspect, the first and second DNA segments are located in tandem on the same nucleic acid molecule. In a more preferred aspect, the first and second DNA segments are located on different chromosomes or at least not in tandem on the same chromosome. In a preferred aspect, the first and second DNA segments are separated by at least 2 centiMorgans (cM), 3 cM, 5 cM, 10 cM, 25 cM, or 50 cM. In another aspect, the plant genome also includes a fifth shorter transcribable nucleic acid sequence homologous to a portion of the second transcription unit located outside of a second DNA segment and adjacent to the second left border region. In an aspect, the fourth shorter transcribable nucleic acid sequence can or cannot have a separate promoter from the second transcription unit. Nucleic acid molecules of the present invention are shown in FIGS. 4 and 5. In another aspect, the shorter transcribable nucleic acid sequence can be located in the 5' UTR or 3' UTR of the second transcription unit, such as shown in FIGS. 9 and 10. In another aspect, the shorter transcribable nucleic acid sequence can or cannot be synthetic, such as shown in FIGS. 9-12.

d. Plants

In an aspect, the present invention includes a nucleic acid molecule of the present invention within a plant. Plants that can be made by practice of the present invention include any plants that are subject to transformation and regeneration and include, but are not limited to, *Acacia*, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, cauliflower, celery, Chinese cabbage, cherry, cilantro, citrus, clementines, coffee, corn, cotton, cucumber, Douglas fir, eggplant, endive, escarole, eucalyptus, fennel, figs, forest trees, gourd, grape, grapefruit, honey dew, jicama, kiwifruit, lettuce, leeks, lemon, lime, Loblolly pine, mango, melon, mushroom, nut, oat, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet corn, sweet potato, sweetgum, tangerine, tea, tobacco, tomato, turf, a vine, watermelon, wheat, yams, and zucchini. In preferred embodiments, the plant is a bean, broccoli, cabbage, canola, carrot, cauliflower, celery, Chinese cabbage, corn, cotton cucumber, eggplant, leek, lettuce, melon, pea, pepper, pumpkin, radish, spinach, soybean, squash, sugarcane, sweet corn, tomato, watermelon, and wheat plant. In particular embodiments, the plant is a corn plant. In particular aspects, the plant is a soybean plant. In other aspects, the plant is a cotton plant. And in still further embodiments, the plant is a canola plant.

In an aspect, the present invention includes a genome of the present invention within a plant. In an aspect, the present invention includes a plant with a plant genome having a nucleic acid molecule including a first DNA segment including a first transcription unit including a sequence of interest flanked on both sides by a first and second shorter transcribable nucleic acid sequences in opposite orientation to each other and located between a first left border region and a first right border region, where the first and second transcribable nucleic acid sequences are physically linked to the first border regions and the first border regions flank the first DNA segment; and a second DNA segment including a second transcription unit including a selectable marker gene flanked on both sides by a third and fourth shorter transcribable nucleic acid sequence in opposite orientation to each other and located between a second left border region and a second right border region, where the third and fourth shorter transcribable nucleic acid sequences are physically linked to the second border regions and the second border regions flank the second DNA segment, and the third shorter transcribable nucleic acid sequence is physically linked and operably linked to a promoter; where the first, second, third and fourth shorter transcribable nucleic acid sequences are homologous to a portion of the second transcription unit. In a preferred aspect, the first transcription unit does not share any sequence identity with 21 or more contiguous nucleotides to a shorter transcribable nucleic acid sequence. In another aspect, the plant also includes a fifth shorter transcribable nucleic acid sequence homologous to a portion of the second transcription unit located outside of a DNA segment and adjacent to the second left border and can also include a third transcription unit with a non-lethal negative selectable marker gene located outside of a DNA segment.

In a more preferred aspect, the present invention includes a plant with a plant genome having a nucleic acid molecule including a first DNA segment including a first transcription unit including a sequence of interest flanked on both sides by a first and second shorter transcribable nucleic acid sequences in opposite orientation to each other and located between a first left border region and a first right border region, where the first and second transcribable nucleic acid sequences are physically linked to the first border regions and the first border regions flank the first DNA segment; and a second DNA segment including a second transcription unit including a selectable marker gene flanked on both sides by a third and fourth shorter transcribable nucleic acid sequence in opposite orientation to each other and located between a second left border region and a second right border region, where the third and fourth shorter transcribable nucleic acid sequences are physically linked to the second border regions and the second border regions flank the second DNA segment, and the third shorter transcribable nucleic acid sequence is physically linked and operably linked to a promoter; where the first, second, third and fourth shorter transcribable nucleic acid sequences are homologous to a portion of the second transcription unit, and said nucleic acid molecule further contains a fifth shorter transcribable nucleic acid sequence that is homologous to a portion of the second transcription unit located between the first DNA segment and the second DNA segment and adjacent to the second left border region. This plant can also include a third transcription unit with a non-lethal negative selectable marker gene located outside of a DNA segment.

In an aspect, the present invention includes a plant with a plant genome having a nucleic acid molecule including a first DNA segment including a first transcription unit including a sequence of interest flanked on both sides by a first and second shorter transcribable nucleic acid sequences in opposite orientation to each other and located between a first left border region and a first right border region, where the first and second transcribable nucleic acid sequences are physically linked to the first border regions and the first border regions flank the first DNA segment; and a second DNA segment including a second transcription unit including a selectable marker gene flanked on both sides by a third and fourth shorter transcribable nucleic acid sequence in opposite orientation to each other and located between a second left border region; where the first and second shorter transcribable nucleic acid sequences are homologous to a portion of the second transcription unit and said plant genome lacks the second transcription unit. This plant can also include a third transcription unit with a non-lethal negative selectable marker gene located outside of the DNA segment.

In a more preferred aspect, the present invention includes a plant with a plant genome having a nucleic acid molecule including a first DNA segment including a first transcription unit including a sequence of interest flanked on both sides by a first and second shorter transcribable nucleic acid sequences in opposite orientation to each other and located between a first left border region and a first right border region, where the first and second transcribable nucleic acid sequences are physically linked to the first border regions and the first border regions flank the first DNA segment; and a second DNA segment including a second transcription unit including a selectable marker gene flanked on both sides by a third and fourth shorter transcribable nucleic acid sequence in opposite orientation to each other and located between a second left border region; where the first and second shorter transcribable nucleic acid sequences are homologous to a portion of the second transcription unit and said plant genome lacks the second transcription unit including a selectable marker gene. In a preferred aspect, a shorter transcribable nucleic acid sequence does not share any sequence identity with greater than 21 nucleotides of the first transcription unit. In another preferred aspect, the present invention includes a plant lacking a selectable marker gene. The plant can further contain a fifth shorter transcribable nucleic acid sequence that is homologous to a portion of the second transcription unit not located between the first DNA segment or the second DNA segment and adjacent to the second left border region. This plant can also include a third transcription unit with a non-lethal negative selectable marker gene located outside of a DNA segment.

e. Transgenic Cell

In an aspect, the present invention includes a nucleic acid molecule of the present invention within a transgenic cell. A transgenic cell has exogenous nucleic acids.

Nucleic acids include deoxynucleic acids (DNA) and ribonucleic acids (RNA) and functionally equivalent analogues thereof. Exemplary nucleic acids that may be introduced by the methods encompassed by the present invention include, for example, nucleic acid sequences or genes from another species, or even genes or sequences that originate with or are present in the same species, but are incorporated into recipient cells by genetic engineering methods rather than classical reproduction or breeding techniques.

The term "exogenous" is also intended to refer to genes that are not normally present in the cell being transformed, or perhaps simply not present in the form, structure, etc., as found in the transforming nucleic acid segment or gene, or genes that are normally present yet that one desires, e.g., to have over-expressed. The term "exogenous" gene or nucleic acid is intended to refer to any gene or nucleic acid segment that is introduced into a recipient cell, regardless of whether a similar gene may already be present in such a cell. The type of nucleic acid molecule included in the exogenous nucleic acid molecule can include a nucleic acid sequence that is already present in the cell, a nucleic acid sequence from another plant, a nucleic acid sequence from a different organism, or a nucleic acid sequence generated externally, such as a nucleic acid sequence including an antisense or RNAi message of a gene, or a nucleic acid sequence encoding a synthetic or modified version of a gene.

The present invention includes any bacterial cell having a nucleic acid molecule of the present invention. Such a bacterial cell may even only be involved in the propagation of a nucleic acid molecule of the present invention. In particular, bacteria known to mediate plant cell transformation include a number of species of the Rhizobiaceae, including, but not limited to, *Agrobacterium* sp., *Sinorhizobium* sp., *Mesorhizobium* sp., and *Bradyrhizobium* sp. (e.g. Broothaerts et al., 2005; US20050289667; US20050289672; US20070271627). Targets for such transformation have often been undifferentiated tissues, although differentiated tissue also has been used for transient and stable plant transformation, and may be in this instance. Examples of these tissues include embryos including immature embryos, callus, cotyledons, hypocotyls, meristems, leaves, stems, or roots. Other methods have been developed for transferring genes into plant tissue including high velocity microprojection, microinjection, electroporation, direct DNA uptake and, bacterially-mediated transformation. Where non-bacterially mediated transformation is used, the nucleic acids of the present invention may not include a border region.

In a preferred aspect, the present invention includes a bacterial cell having a nucleic acid molecule of the present invention. In a more preferred aspect, the bacterial cell is competent for the transformation of at least a first plant cell. In a most preferred aspect, the bacterial cell is any one of *Agrobacterium* spp., *Rhizobium* spp., *Sinorhizobium* spp., *Mesorhizobium* spp., *Phyllobacterium* spp., *Ochrobactrum* spp., *Bradyrhizobium* spp., *Pseudomonas* spp, *Azospirillum* spp, *Rhodococcus* spp, *Phyllobacterium* spp, *Xanthomonas* spp, *Burkholderia* spp, *Erwinia* spp, *Ochrobacter* spp, and *Bacillus* spp. In a preferred aspect, the present invention includes a plant cell. In a more preferred aspect, the cell is a bean, broccoli, cabbage, canola, carrot, cauliflower, celery, Chinese cabbage, corn, cotton cucumber, eggplant, leek, lettuce, melon, pea, pepper, pumpkin, radish, spinach, soybean, squash, sugarcane, sweet corn, tomato, watermelon, and wheat cell. In a most preferred aspect, the plant cell is a sugarcane, wheat, corn, soybean, cotton, or canola, plant cell.

Methods of transforming plant cells are well known by persons of ordinary skill in the art. For instance, specific instructions for transforming plant cells by microprojectile bombardment with particles coated with recombinant DNA are found in U.S. Pat. Nos. 5,015,580 (soybean); 5,550,318 (corn); 5,538,880 (corn); 5,914,451 (soybean); 6,160,208 (corn); 6,399,861 (corn) and 6,153,812 (wheat); 6,002,070 (rice); 7,122,722 (cotton); 6,051,756 (Brassica); 6,297,056 (Brassica); US Patent Publication 20040123342 (sugarcane) and *Agrobacterium*-mediated transformation is described in U.S. Pat. Nos. 5,159,135 (cotton); 5,824,877 (soybean); 5,591,616 (corn); 6,384,301 (soybean); 5,750,871 (Brassica); 5,463,174 (Brassica) 5,188,958 (Brassica), all of which are incorporated herein by reference. Methods for transforming other plants can be found in Compendium of Transgenic Crop Plants, 2009. Blackwell Publishing.

In an aspect, the present invention includes a transgenic cell transformed with a nucleic acid molecule including a first DNA segment including a first transcription unit flanked on both sides by a first and second shorter transcribable nucleic acid sequences in opposite orientation to each other and located between a first left border region and a first right border region, where the first and second transcribable nucleic acid sequences are physically linked to the first border regions and the first border regions flank the first DNA segment; and a second DNA segment including a second transcription unit flanked on both sides by a third and fourth shorter transcribable nucleic acid sequence in opposite orientation to each other and located between a second left border region and a second right border region, where the third and fourth shorter transcribable nucleic acid sequences are physically linked to the second border regions and the second border regions flank the second DNA segment, and the third shorter transcribable nucleic acid sequence is physically linked and operably linked to a promoter; where the first, second, third and fourth shorter transcribable nucleic acid sequences are homologous to a portion of the second transcription unit.

In an aspect, the present invention includes a transgenic cell transformed with a nucleic acid molecule including a first DNA segment including a first transcription unit flanked on both sides by a first and second shorter transcribable nucleic acid sequences in opposite orientation to each other and located between a first left border region and a first right border region, where the first and second transcribable nucleic acid sequences are homologous to a portion of a second transcription unit and are physically linked to the first border regions and the first border regions flank the first DNA segment.

In an aspect, the present invention includes a cell transformed with a nucleic acid molecule including a DNA segment including a transcription unit flanked on both sides by a first and second shorter transcribable nucleic acid sequence in opposite orientation to each other and located between a left border region and a right border region, where the first and second shorter transcribable nucleic acid sequences are physically linked to the border regions and the border regions flank the DNA segment, and the first shorter transcribable nucleic acid sequence is physically linked and operably linked to a promoter and the first and the second shorter transcribable nucleic acid sequences are homologous to a portion of the transcription unit. In a preferred aspect, the present invention includes a transgenic cell lacking a selectable marker gene.

Examples of desirable traits for transcription units include but are not limited to genes for disease, insect, or pest tolerance, herbicide tolerance, genes for quality improvements such as yield, nutritional enhancements, environmental or stress tolerances, or any desirable changes in plant physiology, growth, development, morphology or plant product(s). Nonlimiting examples are listed in Table 1.

TABLE 1

List of sequence or gene of interest and traits they confer.

| Trait | Sequence or gene of interest | Reference |
|---|---|---|
| Male/female sterility system | Several | US20050150013 |
| | Glyphosate/EPSPS | U.S. Pat. No. 6,762,344 |
| | Male sterility gene linked to herbicide resistant gene | U.S. Pat. No. 6,646,186 |
| | Acetylated toxins/deacetylase | U.S. Pat. No. 6,384,304 |
| | Antisense to an essential gene in pollen formation | U.S. Pat. No. 6,255,564 |
| | DNAase or endonuclease/restorer protein | U.S. Pat. No. 6,046,382 |
| | Ribonuclease/barnase | U.S. Pat. No. 5,633,441 |
| Intrinsic yield | glycolate oxidase or glycolate dehydrogenase, glyoxylate carboligase, tartronic semialdehyde reductase | US2006009598 |
| | eukaryotic initiation Factor 5A; deoxyhypusine synthase | US20050235378 |
| | zinc finger protein | US20060048239 |
| | methionine aminopeptidase | US20060037106 |
| | several | US20060037106 |
| | 2,4-D dioxygenase | US20060030488 |
| | serine carboxypeptidase | US20060085872 |
| | Several | USRE38,446; 6,716,474; 6,663,906; 6,476,295; 6,441,277; 6,423,828; 6,399,330; 6,372,211; 6,235,971; 6,222,098; 5,716,837; 6,723,897; 6,518,488 |
| Nitrogen use efficiency | fungal nitrate reductases, mutant nitrate reductases lacking post-translational regulation, glutamate synthetase-1, glutamate dehydrogenase, aminotransferases, nitrate transporters (high affinity and low affinities), ammonia transporters and amino acid transporters | US20050044585 |
| | glutamate dehydrogenase | US20060090219 |
| | cytosolic glutamine synthetase; root-specific glutamine synthetase. | EP0722494 |
| | several | WO05103270 |
| | glutamate 2-oxoglutarate aminotransferase | U.S. Pat. No. 6,864,405 |
| Abiotic Stress tolerance including cold, heat, drought | succinate semialdehyde dehydrogenase | US20060075522 |
| | several | WO06032708 |
| | several | US20060008874 |
| | transcription factor | US20060162027 |
| Disease resistance | CYP93C (cytochrome P450) | U.S. Pat. No. 7,038,113 |
| | Several | U.S. Patents U.S. Pat. Nos. 7,038,113; 6,653,280; 6,573,361; 6,506,962; 6,316,407; 6,215,048; 5,516,671; 5,773,696; 6,121,436; 6,316,407; 6,506,962; 6,617,496; 6,608,241; 6,015,940; 6,013,864; 5,850,023; 5,304,730); 6,228,992; 5,516,671 |
| Insect resistance | Cry1Aa, Cry1Ab, Cry1Ac, Cry1Ba, Cry1Bb, Cry1Ca, Cry2Aa, Cry2Ab, Cry3A, Cry3B, Cry3C, Cry9, Cry34 and Cry35 (PS149B1), ET33, ET34, ET29, TIC 809, TIC810, TIC900, TIC901, TIC1201, TIC407, TIC417, PS149B1, VIP1, VIP2, VIP3 and VIP3A, Cry1A.105, RNA for gene suppression targeting an insect gene, DV49 | U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; |

TABLE 1-continued

List of sequence or gene of interest and traits they confer.

| Trait | Sequence or gene of interest | Reference |
|---|---|---|
| | | 5,942,664; 5,942,658; 5,880,275; 5,763,245; 5,763,241; 6,291,156; 6,486,157; 6,429,360; 7,244,820; US2005/0210545; US 2007/022897; WO 07/027776; US20060021087; WO07027776A2 |
| Enhanced amino acid content | glutamate dehydrogenase<br>threonine deaminase<br>dihydrodipicolinic acid synthase (dap A) | U.S. Pat. No. 6,969,782<br>US20050289668<br>U.S. Pat. No. 5,258,300 |
| Enhanced protein content | Several | US20050055746; U.S. Pat. No. 6,380,466 |
| Modified fatty acids | Several | U.S. Pat. No. 6,949,698; U.S. Pat. Nos. 6,444,876; 6,426,447; 6,380,462; U.S. Patents U.S. Pat. Nos. 6,949,698; 6,828,475; 6,822,141; 6,770,465; 6,706,950; 6,660,849; 6,596,538; 6,589,767; 6,537,750; 6,489,461; 6,459,018 |
| Enhanced oil content | Several | U.S. Pat. Nos. 6,495,739; 5,608,149; 6,483,008; 6,476,295 |
| Carbohydrate production | Raffinose saccharides | U.S. Pat. No. 6,967,262 |
| Starch production | Several | U.S. Pat. Nos. 6,951,969; 6,538,181; 6,538,179; 6,538,178; 5,750,876; 6,476,295 |
| Phytic acid reduction | inositol polyphosphate 2-kinase<br>inositol 1,3,4-triphosphate 5/6-kinases | WO06029296<br>US20050202486 |
| Processing enzymes production | Several<br>Alpha-amylase<br>phytase | WO05096804; U.S. Pat. No. 5,543,576<br>US20060200877<br>US20030170293 |
| Biopolymers | Several | U.S. Patents USRE37,543; 6,228,623; 5,958,745 and U.S. Pat. Publication No. US20030028917 |
| Enhanced nutrition | Several | U.S. Pat. Nos. 6,723,837; 6,653,530; 6,5412,59; 5,985,605; 6,171,640 |
| Pharmaceutical peptides and secretable peptides | Several | U.S. Pat. Nos. 6,812,379; 6,774,283; 6,140,075; 6,080,560 |
| Improved processing trait | sucrose phosphorylase | U.S. Pat. No. 6,476,295 |
| Improved digestibility | thioredoxin and/or thioredoxin reductase | U.S. Pat. No. 6,531,648 |

In a preferred aspect, the sequence of interest in the second transcription unit is a marker gene such as a selectable, screenable, or scoreable marker gene. In one aspect, a marker gene is capable of identifying a transformed cell. In one aspect, a marker gene may function in a regenerable plant tissue to produce a compound that would confer upon the plant tissue resistance to an otherwise toxic compound. A number of marker genes are known in the art and can be used in the present invention. Sequences of interest for use as a selectable, screenable, or scoreable marker would include but are not limited to GUS, green fluorescent protein (GFP), luciferase (LUX), genes conferring tolerance to antibiotics like kanamycin (Dekeyser et al., 1989), neomycin, paromomycin, G418, aminoglycosides, spectinomycin, streptomycin, hygromycin B, bleomycin, phleomycin, sulfonamides, streptothricin, chloramphenicol, methotrexate, 2-deoxyglucose, betaine aldehyde, S-aminoethyl L-cysteine, 4-methyltryptophan, D-xylose, D-mannose, benzyladenine-N-3-glucuronidase. Examples of various selectable markers and genes providing resistance against them are disclosed in Miki and McHugh, 2004 (Miki and McHugh, J. Biotechnol., 107: 193-232, 2004). Genes that encode enzymes that give tolerance to herbicides can also be used as marker genes. Examples of these herbicides include glyphosate (e.g. 5-enolpyruvylshikimate-3-phosphate synthase (EPSPS): Della-Cioppa et al., 1987; U.S. Pat. No. 5,627,061; U.S. Pat. No. 5,633,435; U.S. Pat. No. 6,040,497; U.S. Pat. No. 5,094,945; WO04074443, and WO04009761; glyphosate oxidoreductase (GOX; U.S. Pat. No. 5,463,175); glyphosate decarboxylase (WO05003362 and US Patent Application 20040177399) or glyphosate N-acetyltransferase (GAT; U.S. Patent Publication 20030083480)), dalapon (e.g. dehl encoding 2,2-dichloropropionic acid dehalogenase conferring tolerance to 2,2-dichloropropionic acid (Dalapon; WO9927116)), bromoxynil (haloarylnitrilase (Bxn) for conferring tolerance to bromoxynil (WO8704181A1; U.S. Pat.

No. 4,810,648; WO8900193A)), sulfonyl herbicides (e.g. acetohydroxyacid synthase or acetolactate synthase conferring tolerance to acetolactate synthase inhibitors such as sulfonylurea, imidazolinone, triazolopyrimidine, pyrimidyloxybenzoates and phthalide; (U.S. Pat. Nos. 6,225,105; 5,767, 366; 4,761,373; 5,633,437; 6,613,963; 5,013,659; 5,141,870; 5,378,824; 5,605,011)); encoding ALS, GST-II), bialaphos or phosphinothricin or derivatives (e.g phosphinothricin acetyltransferase (bar) conferring tolerance to phosphinothricin or glufosinate (U.S. Pat. Nos. 5,646,024, 5,561,236, 5,276,268; 5,637,489; 5,273,894; and EP 275,957)), atrazine (encoding GST-III), dicamba (dicamba monooxygenase; U.S. Patent Application Publications 20030115626, 20030135879), or sethoxydim (modified acetyl-coenzyme A carboxylase for conferring tolerance to cyclohexanedione (sethoxydim) and aryloxyphenoxypropionate (haloxyfop) (U.S. Pat. No. 6,414, 222), herbicide containing an aryloxyalkanoate moiety such as phenoxy auxins such as 2,4-D and dichlorpropand pyridyloxy auxins such as fluoroxypyr and triclopyr (aryloxyphenoxypropionates (AOPP) aryloxyalkanoate dioxygenase conferring resistance to the said herbicides; WO05 107437; WO07053482), among others. Other selection procedures can also be implemented including positive selection mechanisms (e.g. use of the manA gene of *E. coli*, allowing growth in the presence of mannose) and would still fall within the scope of the present invention.

Nucleic acid molecules of the present invention or fragments thereof are capable of specifically hybridizing to other nucleic acid molecules, also included in the present invention, under certain circumstances. For example, shorter transcribable nucleic acid sequences can be capable of hybridizing to a first or second transcription unit, for example, under high or low stringency. In an aspect, the nucleic acid molecules of the present invention include nucleic acid molecules that hybridize to these molecules, for example, under high or low stringency, that are substantially homologous sequences to these molecules. As used herein, two nucleic acid molecules are capable of specifically hybridizing to one another if the two molecules are capable of forming an anti-parallel, double-stranded nucleic acid structure. As used herein, molecules exhibit "complete complementarity" when every nucleotide of one of the molecules is complementary to a nucleotide of the other. Two molecules are "minimally complementary" if they can hybridize to one another with sufficient stability to permit them to remain annealed to one another under at least conventional "low-stringency" conditions. Similarly, the molecules are "complementary" if they can hybridize to one another with sufficient stability to permit them to remain annealed to one another under conventional "high-stringency" conditions. Conventional stringency conditions are described by Sambrook et al., In: *Molecular Cloning, A Laboratory Manual,* 2nd Edition, Cold Spring Harbor Press, Cold Spring Harbor, N.Y. (1989)), and by Haymes et al., In: *Nucleic Acid Hybridization, A Practical Approach*, IRL Press, Washington, D.C. (1985).

Departures from complete complementarity are therefore permissible, as long as such departures do not completely preclude the capacity of the molecules to form a double-stranded structure. In order for a nucleic acid sequence to serve as a shorter transcribable nucleic acid sequence, it need only be sufficiently complementary in sequence to be able to form a stable double-stranded structure under the particular solvent and salt concentrations employed such that it can serve as a substrate for enzymes to generate small siRNAs or miRNAs.

As used herein, a substantially homologous sequence is a nucleic acid sequence that will specifically hybridize to the complement of the nucleic acid sequence to which it is being compared under high stringency conditions. A shorter transcribable nucleic acid sequence of the present invention can hybridize under stringent conditions to a target DNA sequence. The term "stringent hybridization conditions" is defined as conditions under which a shorter transcribable nucleic acid sequence hybridizes specifically with a target sequence(s) and not with non-target sequences, as can be determined empirically. The term "stringent conditions" is functionally defined with regard to the hybridization of a shorter transcribable nucleic acid sequence to a target nucleic acid (i.e., to a particular nucleic acid sequence of interest) by the specific hybridization procedure discussed in Sambrook et al., 1989, at 9.52-9.55. See also, Sambrook et al., 1989 at 9.47-9.52, 9.56-9.58; Kanehisa, *Nucl. Acids Res.* 12:203-213, 1984; and Wetmur and Davidson, *J. Mol. Biol.* 31:349-370, 1968. Appropriate stringency conditions that promote DNA hybridization are, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y., 1989, 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

For example, stringent hybridization using shorter transcribable nucleic acid sequence can be performed at 65° C. in 6×SSC, 0.5% SDS, 5×Denhardt's, 100 µg/mL nonspecific DNA (e.g., sonicated salmon sperm DNA) with washing at 0.5×SSC, 0.5% SDS at 65° C., for high stringency.

It is contemplated that lower stringency hybridization conditions such as lower hybridization and/or washing temperatures can be used to identify related sequences having a lower degree of sequence similarity if specificity of binding of the shorter transcribable nucleic acid sequence to target sequence(s) is preserved. Accordingly, the nucleotide sequences of the present invention can be used for their ability to selectively form duplex molecules with complementary stretches of DNA, RNA, or cDNA fragments. Detection of DNA segments via hybridization is well-known to those of skill in the art, and thus depending on the application envisioned, one will desire to employ varying hybridization conditions to achieve varying degrees of selectivity of probe towards target sequence and the method of choice will depend on the desired results.

The agents of the present invention may also be recombinant. As used herein, the term recombinant means any agent (e.g. DNA, peptide etc.), that is, or results, however indirect, from human manipulation of a nucleic acid molecule.

In an aspect, an agent of the present invention will specifically hybridize to one or more of the nucleic acid molecules set forth in the present invention or fragments of either under moderately stringent conditions, for example at about 2.0× SSC and about 65° C. In an aspect, a nucleic acid of the present invention will specifically hybridize to one or more of the nucleic acid molecules set forth in the present invention or fragments thereof under high stringency conditions.

Agents of the present invention include fragment nucleic acid molecules of the present invention. Fragments can contain significant portions of, or indeed most of, nucleic acid molecules set forth in the present invention. In an aspect, the fragments are between 100 and 200 contiguous residues, 75 and 100 contiguous residues, 50 and 150 contiguous residues, or 20 and 50 contiguous residues long of a nucleic molecule of the present invention. In another aspect, the fragment comprises at least 20, 21, 22, 23, 24, 25, 50, 75, 100, or 200 contiguous residues of a nucleic acid molecule of the present invention and 100, 200, 300, 400, 500 at most contiguous residues of a nucleic acid molecule of the present invention. In an aspect, a fragment nucleic acid molecule is capable of selectively hybridizing to nucleic acid molecules set forth in the present invention.

In one aspect of the present invention, a preferred nucleic acid sequence of the present invention shares between 80% and 100% or 90% and 100% sequence identity across the length of the sequence with a nucleic acid sequence set forth in the present invention or fragments thereof. In a further aspect of the present invention, a preferred nucleic acid sequence of the present invention shares between 95% and 100% sequence identity with a nucleic acid sequence set forth in the present invention or fragments thereof. In an aspect of the present invention, a preferred marker nucleic acid molecule of the present invention shares between 98% and 100% sequence identity with a nucleic acid sequence set forth in the present invention or fragments thereof.

The percent identity is preferably determined using the "Best Fit" or "Gap" program of the Sequence Analysis Software Package™ (Version 10; Genetics Computer Group, Inc., University of Wisconsin Biotechnology Center, Madison, Wis.). "Gap" utilizes the algorithm of Needleman and Wunsch to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman. The percent identity calculations may also be performed using the Megalign program of the LASERGENE bioinformatics computing suite (default parameters, DNASTAR Inc., Madison, Wis.). The percent identity is most preferably determined using the "Best Fit" program using default parameters.

Having now generally described the invention, the same will be more readily understood through reference to the following examples which are provided by way of illustration, and are not intended to be limiting of the present invention, unless expressly specified.

VIII. EXAMPLES

Example 1

This example demonstrates use of an RNAi-selection against linkage construct (RNAi-SAL, pMON97397) or a crtB-selection against readthrough construct (crtB-SAR, pMON108800) for increasing the percentage of one-copy gene of interest (GOI) events as compared to a conventional 2T-DNA control construct (pMON97396). These constructs are made with standard molecular biology methods known to one skilled in the art. The constructs are mobilized in *Agrobacterium tumefaciens* which is then used to obtain transformed corn plants according to the transformation method described by Cai et al. (US Published Application 20040244075), herein incorporated by reference in its entirety. The GOI copy number in an event is estimated by assaying for PinII 3'UTR sequence present in the GOI transcription unit by TaqMan® assay (Applied Biosystems, Foster City, Calif.). As shown in Table 2, the RNAi-SAL and crtB-SAR constructs increased percentage of one-copy events as compared to the control construct.

TABLE 2

| | | % of Events with GOI Copy Number | | | |
|---|---|---|---|---|---|
| Construct | Brief Description | one-copy | two-copies | four-copies | over four |
| pMON97397 | RNAi-SAL | 42% | 16% | 8% | 0% |
| pMON108800 | crtB-SAR | 36% | 21% | 2% | 1% |
| pMON97396 | Conventional 2T | 28% | 24% | 13% | 8% |

Example 2

This example demonstrates use of an RNAi-SAL construct (pMON97397) or a crtB-SAR construct (pMON108800) for increasing the marker-free transformations (MFTF) as compared to a conventional 2T control construct (pMON97396). Percentage of MFTF is defined as number of $R_0$ events with at least one unlinked GOI copy per number of explants. These constructs are made with standard molecular biology methods known to one skilled in the art. The constructs are mobilized in *Agrobacterium tumefaciens*, which is then used to obtain transformed corn plants according to the transformation described by Cai et al. (US Published Application 20040244075). The GOI (GUS) or CP4 copy numbers in an event are estimated by assaying for PinII 3'UTR or CP4 sequence present in the gene of interest of transcription unit or selectable marker transcription unit by TaqMan® assay (Applied Biosystems, Foster City, Calif.). The occurrence of unlinked GOI and selectable marker segments in an event was determined by F1 segregation analysis of the events using the TaqMan® assay. As shown in Table 3, both RNAi-SAL and crtB-SAR constructs increased the MFTF as compared to the control construct for events with low complexity i.e., events with 1 GOI or 1-2 GOI.

TABLE 3

| Construct | Brief Description | Mean MFTF (all GOI) | Mean MFTF (1-2 GOI) | Mean MFTF (1 GOI) |
|---|---|---|---|---|
| pMON97396 | Conventional 2T | 2.7% | 1.9% | 0.8% |
| pMON108800 | crtB-SAR | 1.9% | 1.9% | 1.5% |
| pMON97397 | RNAi SAL | 2.9% | 2.5% | 1.9% |

Example 3

This example demonstrates use of a crtB-SAR (pMON108800) construct for reducing readthrough linkage as compared to a conventional 2T construct (pMON97396). These constructs are made with standard molecular biology methods known to one skilled in the art. The constructs were mobilized in *Agrobacterium tumefaciens*, which is then used to obtain transformed corn plants according to the transformation described by Cai et al. (US Published Application 20040244075). The occurrence of unlinked segments in an event is assayed by F1 segregation analysis, and the occurrence of readthrough linkage is assayed for the presence of origin of replication (OriV) DNA between the left border regions of the two segments by TaqMan® assay (Applied Biosystems, Foster City, Calif.). Use of the crtB-SAR construct results in 76% of the events being OriV negative, whereas with the control construct 38% of the events are OriV negative.

Example 4

Constructs described above are further modified to combine both SAL/SAR effects and improve efficiency of eliminating linked events further by selecting against events that have border to border linkage and/or readthrough border linkage.

No transformation events are recovered with RB-RB linked segments from the above constructs and providing the Cauliflower mosaic virus (CaMV) e35S promoter (P-e35S) near the left border assists in eliminating LB-LB linked segments. The following modifications are made in pMON108847 (FIG. 4), the figwort mosaic virus promoter (P-FMV) near the left border (nLB) is replaced with a P-e35S. Also, an additional shorter transcribable nucleic acid sequence is added between the two left borders to prevent the recovery of the events with readthrough linkage.

In pMON108841 (FIG. 5) and pMON108851 (FIG. 6), a 3' UTR of the selectable marker transcription unit is removed such that the transcription of the shorter transcribable nucleic acid sequence is controlled by the promoter of the selectable marker transcription unit thereby eliminating the need for an additional promoter. Also, this improvement makes the shorter transcribable nucleic acid sequence part of the selectable marker transcriptional unit and causes further suppression of the selectable marker gene. An additional fifth shorter transcribable nucleic acid sequence is added to pMON108841 (FIG. 5) between the two left borders to prevent the recovery of the events with readthrough linkage.

These constructs are made with standard molecular biology methods known to one skilled in the art. The constructs are mobilized in *Agrobacterium tumefaciens*, which is then used to obtain transformed corn plants according to the transformation described by Cai et al. (US Published Application 20040244075). The occurrence of readthrough linkage is assayed for the presence of origin of replication (OriV) between the left border regions of the two segments by Taq-Man® assay (Applied Biosystems, Foster City, Calif.). Transformation of pMON108851 occurs subsequent to or simultaneously with pMON108849, which includes a sequence of interest transcription unit.

As shown in Table 4, all RNAi SAL/SAR constructs show a reduction in TF relative to the control by exhibiting lower tissue culture to soil conversion rates than the control due to the loss of events having either type of linkage. Such linkage events are not able to survive on tissue culture selection medium due to silencing and/or weak expression of the selectable marker CP4 in such events. All modified constructs produce higher percentages of OriV− events compared to the control. Further, the presence of the SAR element (as measured by OriV+ events) lowers CP4 expression in one-copy events obtained from transformation with SAR-containing constructs. See Table 4. CP4 expression is measured by Taqman® assay (Applied Biosystems, Foster City, Calif.).

Example 5

Some of the plants recovered after transformation with pMON97397 do not have readthrough linkage, i.e., they are OriV negative, and they have DNA segments linked at left border to left border (LB-LB). Although, the CP4 expression is reduced in these events, it is not sufficiently reduced to prevent recovery of the events containing LB-LB linked segments.

CP4 expression in these events correlates with the length of the loop between the two shorter transcribable nucleic acid sequences and with deletions in the shorter transcribable nucleic acid sequences, i.e., a larger loop size and/or deletion reduced silencing leads to increased CP4 expression. A smaller loop and/or an intact shorter transcribable nucleic acid sequence will enhance silencing further and decrease CP4 expression further.

The constructs described above are modified accordingly. The pMON97397 construct is modified by inserting a 126 basepair non-functional fragment of the octopine type LB (oLB) into the 5'UTR (pMON108883) or 3' UTR (pMON108882) of the CP4 transcription unit, as well as using this fragment to replace the CP4 coding region fragments adjacent to the CP4 RB and LB, and GOI RB. pMON108847 is also modified in the same manner as pMON97367, with one additional modification, the LB fragment is inserted in between two left borders to prevent readthrough linkage (pMON108876 (3' UTR) and pMON108878 (5' UTR)). These modifications are designed to provide a smaller loop for the inverted repeats because the RNAi target is closer to the GOI LB nick site. This also increases the size of the shorter transcribable nucleic acid sequence to allow for more efficient silencing.

These constructs are made with standard molecular biology methods known to one skilled in the art. The constructs are mobilized in *Agrobacterium tumefaciens*, which is then used to obtain transformed corn plants according to the transformation described by Cai et al. (US Published Application 20040244075). The occurrence of unlinked segments in an event is assayed by F1 segregation analysis and the occurrence of readthrough linkage is assayed for the presence of origin of replication, OriV, DNA between the left border regions of the two segments by TaqMan® assay (Applied Biosystems, Foster City, Calif.).

TABLE 4

| Constructs pMON | Brief Description | Average TF (%) | Tissue Culture to Soil Conversion Rate | OriV− Events | Average CP4 expression | | |
|---|---|---|---|---|---|---|---|
| | | | | | OriV− | OriV+ | Ratio |
| 108841 | RNAi-SAL e35S (T-less)/SAR | 3.6 | 34% | 88% | 1282110 | 261080 | 4.9 |
| 108847 | RNAi-SAL 2x e35S/SAR | 8.2 | 49% | 75% | 92944902 | 333101 | 279.0 |
| 108849 + 108851 | RNAi-SAL e35S (T-less) LHR/crtB-SAR | 8.0 | 38% | 90% | — | — | — |
| 97396 | Conventional 2T | 18.8 | 77% | 63% | 11849044 | 28400680 | 0.4 |

TABLE 5

| Construct | Brief Description |
|---|---|
| pMON108882 | RNAi-SAL FMV/e35S with modified LB in 3'UTR |
| pMON108883 | RNAi-SAL FMV/e35S with modified LB in 5'UTR |
| pMON108876 | RNAi-SAL 2xe35S with modified LB in 3'UTR/SAR |
| pMON108878 | RNAi-SAL 2xe35S with modified LB in 5'UTR/SAR |

Example 6

This example illustrates the use of a synthetic shorter transcribable nucleic acid sequence instead of a part of the coding region of a selectable marker gene, a regulatory sequence of the transcription unit, or a fragment of the LB sequence in selecting against events that had border to border linkage and/or readthrough border linkage. Synthetic shorter transcribable nucleic acid sequences are desirable for commercial applications over a fragment of a protein coding gene, e.g., such as CP4, flanking a GOI as the presence of such a fragment of a protein coding gene as the shorter transcribable nucleic acid sequence may raise regulatory concerns. To alleviate this concern, sequences that cannot potentially encode proteins are utilized. These synthetic sequences have no protein coding potential by themselves and have no homology to any other transgene or endogenous gene sequence. The use of synthetic transcribable sequences has several advantages. The sequences can be screened for optimal silencing efficacy beforehand. These synthetic shorter transcribable nucleic acid sequences have 75 basepairs, a high Reynolds scores (Reynolds scores represent the potential efficacy of theoretical siRNAs generated from the synthetic sequences for silencing; Reynolds et al., *Nat. Biotechnol.* (2004) 22:326-30), lack ATGs (start codons) in both strands, lack putative polyA signals, and lack potential allergenic peptides. These sequences are inserted into one of the UTRs of the selectable marker transcription unit. A part of it or all of it is also used at the ends of T-DNAs to form the inverted repeats if/when T-DNAs become linked. The effect of the synthetic shorter transcribable nucleic acid sequence on its own is tested by first inserting it in the selectable marker transcription unit and then using a transient transformation assay system to assess its impact on the expression of the selectable marker.

A synthetic shorter transcribable nucleic acid sequence (MTI-5; SEQ ID NO:41) is inserted into the selectable marker transcription unit in the 5' UTR (pMON108880) or 3' UTR (pMON108879). MTI-5 (SEQ ID NO:41) is a 100 basepair (bp) synthetic sequence created by joining parts of two previously identified 75 bp sequences and re-screening with the same criteria used for the 75 bp sequences. In pMON108881, the nos terminator DNA sequence from *Agrobacterium tumefaciens* (T-nos) in the CP4 transcription unit and the promoter are removed such that the synthetic shorter transcribable nucleic acid sequence is under the control of CP4 transcription unit promoter. Additionally a synthetic shorter transcribable nucleic acid sequence is provided between the two left borders to prevent the recovery of the events with readthrough linkage.

TABLE 6

| Construct | Brief Description |
|---|---|
| pMON108879 | RNAi-SAL 2xe35S with MTI-5 in 3'UTR/SAR |
| pMON108880 | RNAi-SAL 2xe35S with MTI-5 in 5'UTR/SAR |
| pMON108881 | RNAi-SAL e35S with MTI-5 in 5'UTR (T-nos)/SAR |

These constructs are made with standard molecular biology methods known to one skilled in the art. The constructs are mobilized in *Agrobacterium tumefaciens*, which is then used to obtain transformed corn plants according to the transformation described by Cai et al. (US Published Application 20040244075). The occurrence of unlinked segments in an event is assayed by F1 segregation analysis and the occurrence of readthrough linkage is assayed for the presence of origin of replication, OriV, DNA between the left border regions of the two segments by TaqMan® assay (Applied Biosystems, Foster City, Calif.).

Having illustrated and described the principles of the present invention, it should be apparent to persons skilled in the art that the invention can be modified in arrangement and detail without departing from such principles. We claim all modifications that are within the spirit, scope and concept of the appended claims.

Example 7

The modified DNA constructs, pMON1 and pMON2, contain a gene of interest cassette and a 126 base pair non-functional fragment of the octopine type LB (oLB) into the 3' UTR as in pMON108882 in Example 5. The DNA constructs are made with standard molecular biology methods known to one skilled in the art. The constructs are mobilized in *Agrobacterium tumefaciens*, which is then used to obtain transformed corn plants according to the transformation described by Cai et al. Individual primary transgenic plants are subjected to a variety of molecular assays, including tests for the presence of origin of replication, OriV, DNA between the left border regions of the two segments by TaqMan® assay (Applied Biosystems, Foster City, Calif.), as well as an RNA based TaqMan® assay to determine levels of expression of the CP4 gene. In addition, the occurrence of unlinked segments in an event is assayed by methods described in WO2009055597. As shown in Table 7, a substantial difference in CP4 expression level in single copy CP4 events can be noticed. Both experimental constructs show high levels of CP4 expression, likely due to the presence of extra e35S and FMV promoters on the CP4 gene as compared to control constructs. Expression of CP4 gene in the linked events is 20 times lower than unlinked events indicating suppression of a selectable marker gene, CP4, by the constructs of the present invention.

TABLE 7

Reduction in selectable marker gene expression in linked events measured as average CP4 expression.

| | Average CP4 Expression Level | |
|---|---|---|
| Construct | Linked Events | Unlinked Events |
| pMON1 | 50965 | 1181222 |
| Control | 12590 | 16473 |
| pMON2 | 55760 | 1570444 |
| Control | 15296 | 9649 |

What is claimed is:

1. A nucleic acid molecule comprising
   a first DNA segment comprising a first transcription unit flanked on both sides by a first and a second shorter transcribable nucleic acid sequence in opposite orientation to each other and located between a first left T-DNA border region and a first right T-DNA border region, wherein said first and second shorter transcribable nucleic acid sequences are physically linked to said first border regions and said first T-DNA border regions flank said first DNA segment; and
   a second DNA segment comprising a second transcription unit flanked on both sides by a third and fourth shorter transcribable nucleic acid sequence in opposite orientation to each other and located between a second left T-DNA border region and a second right T-DNA border region, wherein said third and fourth shorter transcribable nucleic acid sequences are physically linked to said second T-DNA border regions and said second T-DNA border regions flank said second DNA segment, and said third shorter transcribable nucleic sequence is operably linked to a plant-expressible promoter;
   wherein said first, second, third and fourth shorter transcribable nucleic acid sequences are each at least 100 contiguous nucleotides in length, and share greater than 90% sequence identity to each other and to a portion of said second transcription unit; and wherein said first and second DNA segments are not identical.

2. The nucleic acid molecule of claim 1, wherein said second and fourth shorter transcribable nucleic acid sequences are operably linked to a transcription unit.

3. The nucleic acid molecule of claim 1, further comprising a promoter operably linked to said fourth shorter transcribable nucleic acid sequence.

4. The nucleic acid molecule of claim 1, wherein said fourth shorter transcribable nucleic acid sequence is operably linked to said second transcription unit.

5. The nucleic acid molecule of claim 1, wherein said second transcription unit does not comprise a termination sequence.

6. The nucleic acid molecule of claim 1, wherein said first transcription unit comprises a sequence of interest and said second transcription unit comprises a selectable marker gene.

7. The nucleic acid molecule of claim 1, wherein said second transcription unit comprises a selectable marker gene.

8. The nucleic acid molecule of claim 7, wherein all of said shorter transcribable nucleic acid sequences are non-natural sequences.

9. The nucleic acid molecule of claim 8, wherein said non-natural shorter transcribable nucleic acid sequences are homologous to portion of said second transcription unit and said portion is located in an untranslated region (UTR) of said selectable marker gene transcription unit.

10. The nucleic acid molecule of claim 9, wherein said UTR is 3' of said selectable marker gene.

11. The nucleic acid molecule of claim 9, wherein said UTR is 5' of said selectable marker gene.

12. The nucleic acid molecule of claim 1, further comprising a fifth shorter transcribable acid sequence sharing greater than 90% sequence identity to said first, second, third and fourth shorter transcribable nucleic acid sequences and to said portion of said second transcription unit, said fifth shorter transcribable nucleic acid sequence is located between said first DNA segment and said second DNA segment, and said fifth shorter transcribable nucleic acid sequence is physically linked to said second left or right T-DNA border region.

13. The nucleic acid molecule of claim 1, wherein said left and right T-DNA border regions are each about 455 nucleotides comprising 25 nucleotide imperfect direct repeats.

14. The nucleic acid molecule of claim 1, further comprising a thirst transcription unit comprising a non-lethal negative selectable marker gene located between said first DNA segment and said second DNA segment.

15. The nucleic acid molecule of claim 14, wherein said non-lethal negative selectable marker gene is a phytoene synthase gene.

16. The nucleic acid molecule of claim 14, wherein said second transcription unit comprises a selectable marker gene and said first transcription unit comprises a sequence of interest.

17. A two-segment DNA transformation system comprising
- a first DNA segment comprising a first transcription unit flanked on both sides by a first and a second shorter transcribable nucleic acid sequence in opposite orientation to each other and located between a first left T-DNA border region and a first right T-DNA border region, wherein said first and second shorter transcribable nucleic acid sequences are physically linked to said first T-DNA border regions and said first T-DNA border regions flank said DNA segment; and
- a second DNA segment comprising a second transcription unit flanked on both sides by a third and a fourth shorter transcribable nucleic acid sequence in opposite orientation to each other and located between a second left T-DNA border region and a second right T-DNA border region, wherein said third and a fourth shorter transcribable nucleic acid sequences are physically linked to said second T-DNA border regions and said second T-DNA border regions flank said second DNA segment, and said third shorter transcribable nucleic acid sequence is operably linked to a promoter;
- wherein said first, second, third and fourth shorter transcribable nucleic acid sequences are each at least 100 contiguous nucleotides in length, and share greater that 90% sequence identity to each other and to a portion of said second transcription unit; wherein said first and second DNA segments are not identical; and wherein said first and second segments are present on separate nucleic acid molecules.

18. The nucleic acid molecule of claim 1, wherein said shorter transcribable nucleic acid sequences are transcribable in both orientations.

19. The nucleic acid molecule of claim 1, wherein said T-DNA borer regions are capable of enabling the transfer of said segments into a genome mediated by *Afrobaterium* or other *Rhizobia*.

20. The nucleic acid molecule of claim 1, wherein said first, second, third and fourth shorter transcribable nucleic acid sequences each share great that 95%, greater that 97%, greater then 98%, greater then 99% sequence identity or 100% sequence identity to said portion of second transcription unit.

21. The nucleic acid molecule of claim 1, wherein said first, second, third, and fourth shorter transcribable nucleic acid sequences are identical to each other and identical to said portion of said second transcription unit.

22. The nucleic acid molecule of claim 1, wherein the transcription of said second and fourth shorter transcribable nucleic acid sequences triggers the silencing if said second transcription unit.

23. The nucleic acid molecule of claim 12, wherein said wherein said fifth shorter transcribable nucleic acid sequence is identical to said first, second, third, and fourth shorter transcribable nucleic acid sequences, and identical to said portion of said second transcription unit.

24. The nucleic acid molecule of claim 22, wherein said first and third shorter transcribable nucleic acid sequences are operably linked to a transcription unit, and the transcription of said first and third shorter transcribable nucleic acid sequences triggers the silencing if said second transcription unit.

25. The nucleic acid molecule of claim 1, wherein said first transcription unit does not share any sequence identity of 21 or more contiguous nucleotides to said shorter transcribable nucleic acid sequences.

26. The nucleic acid molecule of claim 12, wherein said fifth shorter transcribable nucleic acid sequence is in opposite orientation to either said third or fourth shorter transcribable nucleic acid sequence.

27. A plant genome comprising the nucleic acid molecule of claim 1.

28. A method of selecting for unlinked first and second DNA segments in a plant cell, comprising
   a. transforming a plant cell with the nucleic acid molecule of claim 1;
   b. growing said transformed plant cell; and
   c. selecting a transgenic plant cell with expression of a sequence of interest within said second transcription unit.

29. The system of claim 17, wherein said first, second, third and fourth shorter transcribable nucleic acid sequences each share greater than 95%, greater than 97%, greater than 98%, greater than 99% sequence identity or 100% sequence identity to said portion of said second transcription unit.

30. The system of claim 17, wherein said first, second, third, and fourth shorter transcribable nucleic acid sequences are identical to each other and identical to said portion of said second transcription unit.

* * * * *

UNITED STATES PATENT AND TRADEMARK OFFICE
CERTIFICATE OF CORRECTION

PATENT NO. : 8,338,665 B2
APPLICATION NO. : 12/504646
DATED : December 25, 2012
INVENTOR(S) : Larry Gilbertson and Susan Jane Johnson It is certified that error appears in the above-identified patent and that said Letters Patent is hereby corrected as shown below:

In the Claims:

Column 60, Line 45: please add -- a -- after the word "to" and before the word "portion"

Column 61, Line 47: please change "great that" to -- greater than --; please change "greater that" to -- greater than --

Column 61, Line 48: please change "greater then 98%" to -- greater than 98% --; please change "greater then 99%" to -- greater than 99% --

Column 62, Line 7: please change "claim 1" to -- claim 2 --

Column 62, Line 10: please delete "wherein said"

Column 62, Line 20: please change the word "if" to -- of --

Signed and Sealed this
Fifth Day of March, 2013

Teresa Stanek Rea
*Acting Director of the United States Patent and Trademark Office*

UNITED STATES PATENT AND TRADEMARK OFFICE
CERTIFICATE OF CORRECTION

PATENT NO.         : 8,338,665 B2
APPLICATION NO.    : 12/504646
DATED              : December 25, 2012
INVENTOR(S)        : Larry Gilbertson and Susan Jane Johnson Page 1 of 1

It is certified that error appears in the above-identified patent and that said Letters Patent is hereby corrected as shown below:

In the Claims:

Column 59, Line 51: please add -- acid -- after the word "nucleic" and before the word "sequence";

Column 60, Line 65: please change the word "thirst" to -- third --;

Column 61, Line 43: please change the word "borer" to -- border --;

Column 61, Line 44: please change the word "Afrobaterium" to -- Agrobacterium --

Signed and Sealed this
Nineteenth Day of March, 2013

Teresa Stanek Rea
*Acting Director of the United States Patent and Trademark Office*